(12) United States Patent
Wondka et al.

(10) Patent No.: US 8,409,168 B2
(45) Date of Patent: Apr. 2, 2013

(54) PULMONARY OCCLUSAL STENT DELIVERY CATHETER, LOADING SYSTEM AND METHODS OF USE

(75) Inventors: Anthony Wondka, Thousand Oaks, CA (US); Peter P. Soltesz, Henderson, NV (US); Robert Kotmel, Burlingame, CA (US); Nadia Matov, San Jose, CA (US); Thomas Crowder, Santa Rosa, CA (US)

(73) Assignee: Pulmonx Corporation, Redwood City, CA (US)

( * ) Notice: Subject to any disclaimer, the term of this patent is extended or adjusted under 35 U.S.C. 154(b) by 192 days.

(21) Appl. No.: 12/730,932

(22) Filed: Mar. 24, 2010

(65) Prior Publication Data

US 2010/0175693 A1    Jul. 15, 2010

Related U.S. Application Data

(63) Continuation of application No. 11/280,530, filed on Nov. 15, 2005, now abandoned.

(60) Provisional application No. 60/628,856, filed on Nov. 16, 2004.

(51) Int. Cl.
*A61M 31/00* (2006.01)

(52) U.S. Cl. ............ 604/514; 604/35; 604/107.03; 604/164.03; 604/164.13; 604/43; 604/500; 604/101.04; 604/101.03; 604/164.01; 604/171; 604/523; 604/912; 604/516; 128/200.24

(58) Field of Classification Search ............ 604/35, 604/43, 101.02, 101.03, 101.04, 164.01, 604/164.03, 164.13, 171, 523, 912, 915
See application file for complete search history.

(56) References Cited

U.S. PATENT DOCUMENTS

| | | | |
|---|---|---|---|
| 3,322,126 A | 5/1967 | Rusch et al. | |
| 3,498,286 A | 3/1970 | Polanyi et al. | |
| 3,542,026 A | 11/1970 | Bledsoe | |
| 3,669,098 A | 6/1972 | Takahashi | |
| 3,677,262 A | 7/1972 | Zukowski | |
| 3,776,222 A | 12/1973 | Smiddy | |
| 3,866,599 A | 2/1975 | Johnson | |
| 3,913,568 A | 10/1975 | Carpenter | |
| 4,041,936 A | 8/1977 | Carden | |
| 4,327,720 A | 5/1982 | Bronson et al. | |
| 4,327,721 A | 5/1982 | Goldin et al. | |

(Continued)

FOREIGN PATENT DOCUMENTS

| WO | WO 92/10971 | 7/1992 |
|---|---|---|
| WO | WO 92/10971 A1 | 7/1992 |

(Continued)

OTHER PUBLICATIONS

International Search Report and Written Opinion of PCT Application No. PCT/US05/41642, dated Jul. 7, 2008, 8 pages total.

(Continued)

*Primary Examiner* — Vy Q Bui
(74) *Attorney, Agent, or Firm* — Wilson, Sonsini, Goodrich & Rosati

(57) ABSTRACT

Methods, systems and devices are provided for performing lung volume reduction in patients suffering from chronic obstructive pulmonary disease or other conditions where isolation of a lung segment or reduction of lung volume is desired. The methods are minimally invasive with instruments being introduced through the mouth (endotracheally) and rely on isolating the target lung tissue segment from other regions of the lung and occluding various lung passageways with the use of occlusal stents. The occlusal stents are delivered with the use of an occlusal stent delivery system which is loaded with the occlusal stent with the use of an occlusal stent loading system.

7 Claims, 20 Drawing Sheets

U.S. PATENT DOCUMENTS

| | | | |
|---|---|---|---|
| 4,453,545 A | 6/1984 | Inoue |
| 4,468,216 A | 8/1984 | Muto |
| 4,567,882 A | 2/1986 | Heller |
| 4,716,896 A | 1/1988 | Ackerman |
| 4,742,819 A | 5/1988 | George |
| 4,784,133 A | 11/1988 | Mackin |
| 4,819,664 A | 4/1989 | Nazari |
| 4,846,153 A | 7/1989 | Berci |
| 4,850,371 A | 7/1989 | Broadhurst et al. |
| 4,862,874 A | 9/1989 | Kellner |
| 4,896,941 A | 1/1990 | Hayashi et al. |
| 4,949,716 A | 8/1990 | Chenoweth |
| 4,955,375 A | 9/1990 | Martinez |
| 4,958,932 A | 9/1990 | Kegelman et al. |
| 4,961,738 A | 10/1990 | Mackin |
| 4,976,710 A | 12/1990 | Mackin |
| 5,056,529 A | 10/1991 | de Groot |
| 5,143,062 A | 9/1992 | Peckham |
| 5,146,916 A | 9/1992 | Catalani |
| 5,285,778 A | 2/1994 | Mackin |
| 5,309,903 A | 5/1994 | Long |
| 5,331,947 A | 7/1994 | Shturman |
| 5,361,753 A | 11/1994 | Pothmann et al. |
| 5,477,851 A | 12/1995 | Callaghan et al. |
| 5,499,625 A | 3/1996 | Frass et al. |
| 5,598,840 A | 2/1997 | Iund et al. |
| 5,642,730 A | 7/1997 | Baran |
| 5,645,519 A | 7/1997 | Lee et al. |
| 5,653,231 A | 8/1997 | Bell |
| 5,660,175 A | 8/1997 | Dayal |
| 5,676,671 A | 10/1997 | Inoue |
| 5,682,880 A | 11/1997 | Brain |
| 5,707,352 A | 1/1998 | Sekins et al. |
| 5,752,921 A | 5/1998 | Orr |
| 5,830,222 A | 11/1998 | Makower |
| 5,840,064 A | 11/1998 | Liprie |
| 5,957,949 A | 9/1999 | Leonhardt et al. |
| 6,287,290 B1 | 9/2001 | Perkins et al. |
| 6,398,775 B1 | 6/2002 | Perkins et al. |
| 6,527,761 B1 * | 3/2003 | Soltesz et al. ............ 604/516 |
| 6,585,639 B1 | 7/2003 | Kotmel et al. |
| 6,682,520 B2 | 1/2004 | Ingenito |
| 6,709,401 B2 | 3/2004 | Perkins et al. |
| 6,929,637 B2 | 8/2005 | Gonzalez et al. |
| 2006/0162731 A1 | 7/2006 | Wondka et al. |

FOREIGN PATENT DOCUMENTS

| | | |
|---|---|---|
| WO | WO 95/33506 A1 | 12/1995 |
| WO | WO 98/48706 | 11/1998 |
| WO | WO 98/48706 A1 | 11/1998 |

OTHER PUBLICATIONS

International search report and written opinion dated Jul. 7, 2008 for PCT/US2005/041642.

* cited by examiner

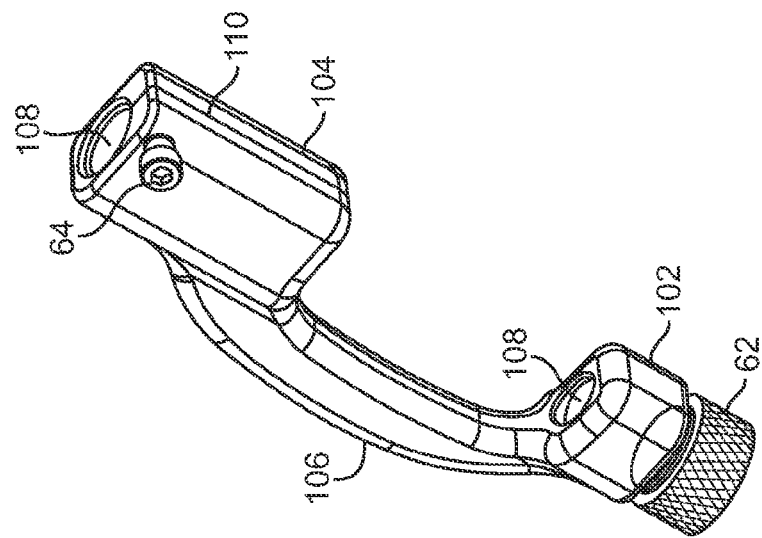
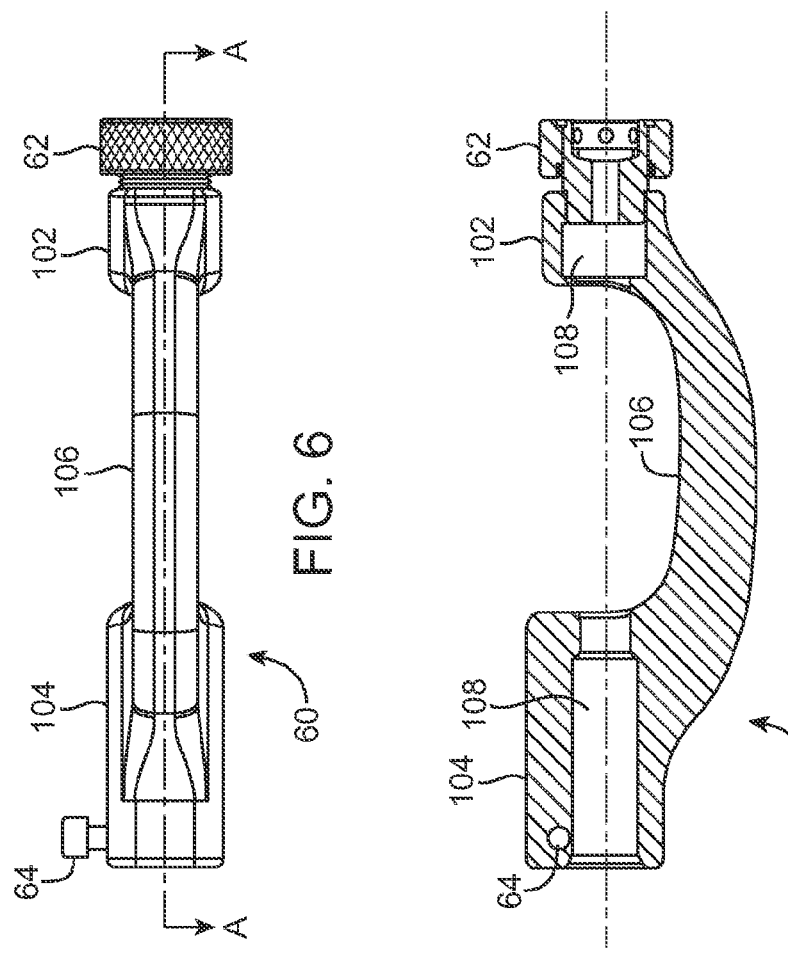

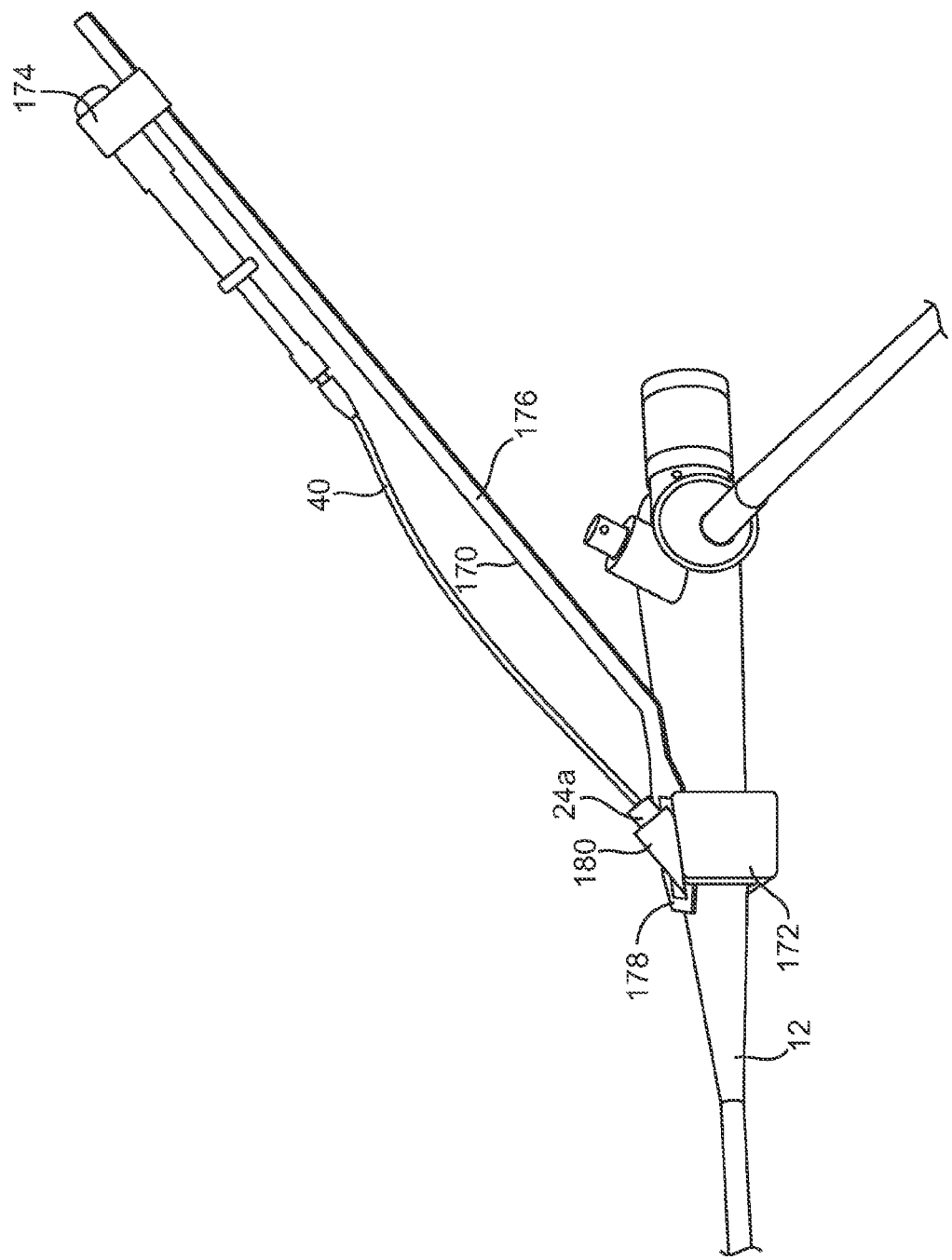

PULMONARY OCCLUSAL STENT DELIVERY CATHETER, LOADING SYSTEM AND METHODS OF USE

CROSS-REFERENCES TO RELATED APPLICATIONS

This application is a continuation of U.S. patent application Ser. No. 11/280,530, filed on Nov. 15, 2005, which claims the benefit of priority of U.S. Provisional Patent Application No. 60/628,856, filed on Nov. 16, 2004, both of which are incorporated herein by reference.

BACKGROUND OF THE INVENTION

1. Field of the Invention

The present invention relates generally to medical devices, systems and methods. In preferred embodiments, the present invention relates to methods and apparatuses for effecting lung volume reduction by aspirating isolated segments of lung tissue.

Chronic obstructive pulmonary disease is a significant medical problem affecting 16 million people or about 6% of the U.S. population. Specific diseases in this group include chronic bronchitis, asthmatic bronchitis, and emphysema. While a number of therapeutic interventions are used and have been proposed, none are completely effective, and chronic obstructive pulmonary disease remains the fourth most common cause of death in the United States. Thus, improved and alternative treatments and therapies would be of significant benefit.

Lung function in patients suffering from some forms of chronic obstructive pulmonary disease can be improved by reducing the effective lung volume, typically by resecting diseased portions of the lung. Resection of diseased portions of the lungs both promotes expansion of the non-diseased regions of the lung and decreases the portion of inhaled air which goes into the lungs but is unable to transfer oxygen to the blood. Lung reduction is conventionally performed in open chest or thoracoscopic procedures where the lung is resected, typically using stapling devices having integral cutting blades. Although these procedures appear to show improved patient outcomes and increased quality of life, the procedure has several major complications, namely air leaks, respiratory failure, pneumonia and death. Patients typically spend approximately 5-7 days in post-op recovery with the majority of this length of stay attributed to managing air leaks created by the mechanical resection of the lung tissue.

In an effort to reduce such risks and associated costs, minimally or non-invasive procedures have been developed. Endobronchial Volume Reduction (EVR) allows the physician to use a catheter-based system to reduce lung volumes. With the aid of fiberoptic visualization and specialty catheters, a physician can selectively collapse a segment or segments of the diseased lung. An occlusal device is then positioned within the lung segment to prevent the segment from reinflating. By creating areas of selective atelectasis or reducing the total lung volume, the physician can enhance the patient's breathing mechanics by creating more space inside the chest wall cavity for the more healthy segments to breath more efficiently.

Additional improvements to EVR are desired. A delivery system is desired which can position an occlusal device within a desired segment of a lung passageway with high accuracy. Such a delivery system should be easy to use, should allow interchangeability of a variety of instruments, and should allow delivery of multiple occlusal devices. It is desired that such delivery of multiple occlusal devices be achieved while maintaining evacuation of a diseased region of the lung. It is also desired to provide a system which utilizes conventional bronchoscopes to deliver the occlusal devices to the lung passageways. Such utilization should be easy to operate and should not interfere with additional therapies which utilize the bronchoscope. At least some of these objectives are met by the current invention.

2. Description of the Background Art

Patents and applications relating to lung access, diagnosis, and treatment include U.S. Pat. Nos. 6,709,401; 6,585,639; 6,527,761; 6,398,775; 6,287,290; 5,957,949; 5,840,064; 5,830,222; 5,752,921; 5,707,352; 5,682,880; 5,660,175; 5,653,231; 5,645,519; 5,642,730; 5,598,840; 5,499,625; 5,477,851; 5,361,753; 5,331,947; 5,309,903; 5,285,778; 5,146,916; 5,143,062; 5,056,529; 4,976,710; 4,955,375; 4,961,738; 4,958,932; 4,949,716; 4,896,941; 4,862,874; 4,850,371; 4,846,153; 4,819,664; 4,784,133; 4,742,819; 4,716,896; 4,567,882; 4,453,545; 4,468,216; 4,327,721; 4,327,720; 4,041,936; 3,913,568 3,866,599; 3,776,222; 3,677,262; 3,669,098; 3,542,026; 3,498,286; 3,322,126; WO 98/48706; WO 95/33506, and WO 92/10971.

BRIEF SUMMARY OF THE INVENTION

The present invention provides methods, systems, and devices for performing lung volume reduction in patients suffering from chronic obstructive pulmonary disease or other conditions where isolation of a lung segment or reduction of lung volume is desired. These methods, systems, and devices are likewise suitable for the treatment of bronchopleural fistula. The methods are minimally invasive with instruments being introduced through the mouth (endotracheally) and rely on isolating the target lung tissue segment from other regions of the lung and occluding various lung passageways with the use of occlusal stents.

In a first aspect of the present invention, an occlusal stent delivery system is provided for delivering an occlusal stent to a target lung passageway. In preferred embodiments, the delivery system includes a visualization instrument configured for endobronchial advancement into a lung passageway leading to the target lung passageway. The instrument having a proximal end, a distal end, a working lumen extending therethrough, means for visualization near the distal end, and an occlusive member disposed near its distal end which is configured to be expandable to occlude the lung passageway. In addition, the system includes a delivery catheter having a proximal end, a distal end and a receptacle formable within its distal end for loading the occlusal stent therein. The delivery catheter is configured to be advanced through the working lumen of the visualization instrument so that its distal end extends beyond the distal end of the visualization instrument and wherein its distal end is retractable so that retraction of its distal end releases the occlusal stent to the target lung passageway. Typically, the distal end of the delivery catheter has portions of variable flexibility to allow the catheter to be advanced through a potentially curved working lumen without applying forces sufficient to redirect the visualization instrument.

In preferred embodiments, the system further includes a clamp connector. In some embodiments, the clamp connector comprises a connector body having a passageway therethrough, and means for connecting the connector body to a visualization instrument having a working lumen so that insertion of an instrument through the passageway of the connector body inserts the instrument into the working lumen of the visualization instrument. In preferred embodiments, the passageway and the working lumen are non-axially aligned during connection. In some embodiments, the clamp connector comprises a connector body having a first end, a second end and an arc-shaped arm connecting the first and second ends, wherein the passageway passes through the first and second arms. However, it may be appreciated that the connector body many have a variety of suitable shapes and forms. Typically, the visualization instrument has a handle to which the connector body is attachable. The means for connecting may have a variety of forms including a fitting, such as a quick connector. In some embodiments, the quick connector comprises a side-action quick connector which allows the connector to be attached and detached from a side approach. Typically, the delivery catheter includes a handle at its distal end and the clamp connector includes a locking mechanism which is capable of locking the handle of the delivery catheter to the clamp connector. Such locking holds the delivery catheter in place in relation to the visualization instrument. In some embodiments, the locking mechanism tightens the passageway through the connector body to hold the at least a portion of the catheter by frictional forces. The locking mechanism may comprises a screw, knob or tensioning lever, among other mechanisms. While the delivery catheter is locked in place, the occlusal stent may be deployed from the delivery catheter by manipulation of the handle of the delivery catheter.

In preferred embodiments, the delivery catheter comprises positioning rod, a tubular shaft extending from its proximal end to its distal end, and a handle positioned at its proximal end. The positioning rod is disposed within the tubular shaft and is fixedly attached to the handle. A receptacle formable within the distal end of the delivery catheter is disposed within the tubular shaft distal of the distal end of the positioning rod. The distance between the distal end of the positioning rod and the distal end of the tubular shaft is the axial length of the receptacle. The tubular shaft is slidable in relation to the positioning rod so that sliding of the tubular shaft shortens the axial length of the receptacle exposing the occlusal stent. When the occlusal stent has a self-expanding design, exposure of the occlusal stent deploys the occlusal stent within the lung passageway. In some embodiments, the occlusal stent is self-expanding in free space to a configuration that has an approximately 11 mm outer diameter. Alternatively, the occlusal stent may be expanded by alternative mechanisms after it has been released into the lung passageway. In either case, the occlusal stent may be comprised of a wire structure or any other type of framework at least partially encapsulated in a polymer. The wire structure is used as an example in the following descriptions but it can be appreciated that the framework can be of a variety of types.

Typically, the positioning rod comprises a main body coil extending along the positioning rod terminating at a plunger tip. In some embodiments, the main body coil has an axial length in the range of approximately 80 to 100 cm and the main body coil is comprised of stainless steel wire.

In some embodiments, the visualization instrument comprises a bronchoscope. It may be appreciated that any suitable bronchoscope may be used, including conventional bronchoscopes. A principal advantage of the present invention is that it allows a user to modify a conventional bronchoscope for use in delivery of occlusal stents in a convenient and economical manner. However, it may also be appreciated that other instruments or catheters may be used which provide viewing or visualization capabilities. Thus, the visualization instrument may further comprise a sheath having a proximal end, a distal end, a lumen extending therethrough and the occlusive member disposed near its distal end, the lumen configured to receive the bronchoscope so that the occlusive member is disposed near the distal end of the bronchoscope. The sheath typically comprises a flexible tubular body having a length in the range from 40 cm to 70 cm, an inside lumen diameter in the range from 1.5 mm to 10 mm, and a wall thickness in the range from 0.2 mm to 0.7 mm.

In a second aspect of the present invention, a loading system is provided. In preferred embodiments, the loading system includes an occlusal stent, a loading body, and a loading mandrel. Again, the occlusal stent is transitionable between an expanded configuration and a contracted configuration. The loading body has a wide-mouthed end and a narrow-mouthed end, wherein the wide-mouthed end is configured to receive the occlusal stent in the expanded configuration and the narrow-mouthed end is configured to hold the occlusal stent in the contracted configuration. The loading mandrel has a proximal end, a distal end, and an attachment device disposed near its distal end that is removably attachable to the occlusal stent. The attachment device may be comprised of a hook, clasp, fastener or magnet, to name a few. The mandrel is configured to load the removably attached occlusal stent into the wide-mouthed end and move the occlusal stent to the narrow-mouthed end.

In preferred embodiments, the loading body comprises a loading receptacle within the wide-mouthed end, wherein the loading receptacle is sized to receive the occlusal stent in the expanded configuration. The loading receptacle may have any suitable size or shape. Typically, the loading receptacle is cylindrical in shape and has a diameter in the range of approximately 10 to 13 mm. In addition, loading body comprises a holding tube within the narrow-mouthed end, wherein the holding tube is sized to receive the occlusal stent in the contracted configuration. Similarly, the holding tube may have any suitable size or shape, typically having a cylindrical shape with a diameter in the range of approximately 2 to 2.5 mm. Further, in preferred embodiments, the loading body comprises a restrictor disposed between the loading receptacle and the holding tube, wherein the restrictor has a funnel shape to transition the occlusal stent from the expanded configuration to the contracted configuration. In some embodiments, loading mandrel includes a first marking near its distal end and the loading body includes a second marking near its narrow-mouthed end, wherein alignment of the first marking with the second marking positions the occlusal stent within the narrow-mouthed end.

In some embodiments, the loading system further comprises a delivery catheter having a proximal end, a distal end and a receptacle formable within its distal end for loading the occlusal stent therein. The narrow-mouthed end of the loading body is typically configured to mate with the distal end of the delivery catheter. The occlusal stent may then be moved from the narrow-mouthed end to the receptacle within the distal end of the delivery catheter with the use of the loading mandrel. Further, in some embodiments the catheter is provided pre-positioned to the narrow-mouthed end of the loading body and the occlusal stent is provided pre-positioned and or pre-attached to the wide-mouthed end and or pre-connected to the positioning rod of the catheter.

In a third aspect of the present invention, methods of delivering an occlusal stent to a lung passageway within a lung of a patient are provided. In preferred embodiments, such methods include providing a visualization instrument, wherein the instrument has a proximal end, distal end, a working lumen therethrough, means for visualization near the distal end, and an occlusive member disposed near its distal end which is configured to be expandable to occlude the lung passageway. The visualization device is advanced through a trachea of the patient to a first location with the lung passageway. The lung passageway is then occluded at the first location with the occlusive member and the lung passageway evacuated. The method further includes providing a delivery catheter having a proximal end, a distal end, and an occlusal stent loaded within a receptacle within its distal end. The delivery catheter is advanced through the working lumen of the visualization instrument so that the distal end of the delivery catheter extends beyond the distal end of the visualization instrument to a second location within the lung passageway. The distal end of the delivery catheter is then retracted which releases the occlusal stent from the receptacle at the second location within the evacuated lung passageway.

Such methods may be performed within lung passageways of various dimensions, shapes and branching patterns. For example, lung passageway may be comprised of a main passageway and at least one branch passageway. The first location may be disposed within the main passageway and the second location disposed within one of the at least one branch passageways. Thus, the distal end of the delivery catheter may be steered or guided in various directions as it is advanced beyond the visualization instrument to reach a desired branch passageway.

Typically, the methods further comprise withdrawing the delivery catheter from the visualization instrument after releasing the occlusal stent while the lung passageway remains evacuated. Another delivery catheter having a proximal end, a distal end, and another occlusal stent loaded within a receptacle within its distal end may then be provided. This may be the delivery catheter that was removed with a new occlusal stent loaded therein, or a different delivery catheter that has been preloaded with an occlusal stent. The another delivery catheter is then advanced through the working lumen of the visualization instrument so that the distal end of the another delivery catheter extends beyond the distal end of the visualization instrument to a third location within the evacuated lung passageway. The third location may be disposed within another of the at least one branch passageways.

Again, the delivery catheter typically comprises a tubular shaft extending from its proximal end to its distal end wherein the occlusal stent is disposed within the tubular shaft within the distal end of the catheter. Thus, releasing comprises withdrawing the tubular shaft to expose the occlusal stent. In preferred embodiments, the delivery catheter comprises a handle disposed at its proximal end and the tubular shaft is slidably connected with the handle by a handle button or any other hand-operated feature such as a loop or trigger, henceforth referred to as button. In these embodiments, withdrawing comprises moving the handle button to withdraw the tubular shaft.

In some embodiments, the visualization instrument has a handle section near its proximal end, and the method further comprises connecting a clamp connector to the handle section of the visualization instrument. Typically, the clamp connector has a passageway therethrough so that advancing the delivery catheter comprises passing the distal end of the delivery catheter through the passageway of the clamp connector and into the working lumen of the visualization instrument. The working lumen is typically accessible via an access port, which extends through the proximal end and typically the handle section of the visualization instrument. The clamp connector can attach directly to the working lumen access port or elsewhere on the visualization instrument handle section as described in the following detailed descriptions. Again, the delivery catheter typically comprises a tubular shaft extending from its proximal end to its distal end and a handle disposed at its proximal end. The clamp connector may further include a locking mechanism wherein the method would further comprise actuating the locking mechanism to lock the handle of the delivery catheter to the clamp connector. The handle of the delivery catheter can be provided in a variety of configurations, such as a configuration that does not enter the working channel of the bronchoscope as well as a configuration that can enter the working channel of the bronchoscope, and combinations thereof. The clamp connector can also be provided in many configurations, wherein the clamp connector physically attaches to a portion of the bronchoscope, typically in the handle section and sometimes directly to the access port, and allows access of the catheter to the bronchoscope working channel. The clamp connector can be an item provided separately, or can be provided as an integral piece of the delivery catheter, and can be reusable or disposable.

When the tubular shaft is slidably connected with the handle of the catheter by a handle button, releasing may comprise moving the handle button to withdraw the tubular shaft and expose the occlusal stent. Releasing may also comprise expanding the occlusal stent to occlude the lung passageway.

In a fourth aspect of the present invention, methods are provided for using the loading system. Such methods include providing a loading mandrel having a proximal end, a distal end and an occlusal stent removably attached to its distal end, wherein the occlusal stent is transitionable between an expanded configuration and a contracted configuration. These methods also include providing a loading body having a wide-mouthed end and a narrow-mouthed end, wherein the wide-mouthed end is configured to receive the occlusal stent in the expanded configuration and the narrow-mouthed end is configured to hold the occlusal stent in the contracted configuration. The loading mandrel is positioned within the loading body so that the occlusal stent is near the wide-mouthed end. The loading mandrel is then manipulated to load the occlusal stent into the wide-mouthed end and move the occlusal stent to the narrow-mouthed end within the loading body.

When the loading body comprises a loading receptacle within the wide-mouthed end, manipulating the loading mandrel may comprise moving the loading mandrel relative to the loading body so that the occlusal stent is positioned within the loading receptacle. When the loading body includes a restrictor adjacent to the loading receptacle, manipulating the loading mandrel may comprise moving the loading mandrel relative to the loading body so that the occlusal stent enters the restrictor. And when the loading body includes a holding tube adjacent to the restrictor, manipulating the loading mandrel may comprise moving the loading mandrel relative to the loading body so that the occlusal stent is positioned within the holding tube. In some embodiments, the loading mandrel includes a first marking near its distal end and the loading body includes a second marking near its narrow-mouthed end. In these embodiments, the method may further comprise aligning the first marking with the second marking indicating that the occlusal stent is positioned within the narrow-mouthed end. The methods may further comprise detaching the occlusal stent from the loading mandrel.

A delivery catheter having a proximal end, a distal end and a receptacle formable within its distal end for loading the occlusal stent therein may also be provided. Such methods may then further include transferring the occlusal stent from the narrow-mouthed end of the loading body to the receptacle of the delivery catheter. To accomplish this, the method may further comprise mating the distal end of the delivery catheter with the narrow-mouthed end of the loading body prior to the transferring step. Transferring may also comprise advancing a loading mandrel through the open-mouthed end of the loading body which pushes the occlusal stent into the distal end of the delivery catheter. The delivery catheter loading system and occlusal stent can be provided separately in which case the user may mate the elements for transferring, or the pieces can be provided pre-positioned together or in a mated configuration so that the user only has to transfer the stent into the catheter through the pre-positioned loading system.

It may be appreciated that the delivery system and/or loading system may be used for a variety of applications. For example, components of the delivery system may be used to deliver non-occlusal tracheobronchial stents, bronchopulmonary fistula plugs or stents, or occlusal stents for the treatment of tuberculosis. Further, components of the delivery system may be modified for to deliver vascular stents, vascular grafts or vascular occlusal devices to the vascular system to treat a variety of vascular ailments. Likewise, the loading system may be used to load a variety of stent-like devices within instruments and catheters having a receptacle for receiving the devices. Further, the clamp connector of the present invention may be used for the passage of any suitable instrument therethrough, such as instruments for implant removal, endoluminal injection (such as of a therapeutic agent, a hemostatic agent, etc.), specimen collection (such as for a biopsy), inspection, or other treatment, such a radiation therapy, etc.

Other objects and advantages of the present invention will become apparent from the detailed description to follow, together with the accompanying drawings.

BRIEF DESCRIPTION OF THE DRAWINGS

FIGS. 5, 6-6A, 7 illustrates various views of an embodiment of a clamp connector.

FIGS. 8C-8E illustrate an embodiment of a clamp connector having the form of an elongate holder.

DETAILED DESCRIPTION OF THE INVENTION

Lung volume reduction is performed by collapsing a target lung tissue segment, usually within lobar or sub-lobular regions of the lung which receive air through a single lung passage, i.e., segment of the branching bronchus which deliver to and receive air from the alveolar regions of the lung. Such lung tissue segments are first isolated and then collapsed by aspiration of the air (or other gases or liquids which may be present) from the target lung tissue segment. Lung tissue has a very high percentage of void volume, so removal of internal gases can reduce the lung tissue to a small percentage of the volume which it has when fully inflated, i.e. inflated at normal inspiratory pressures.

Figure 1:
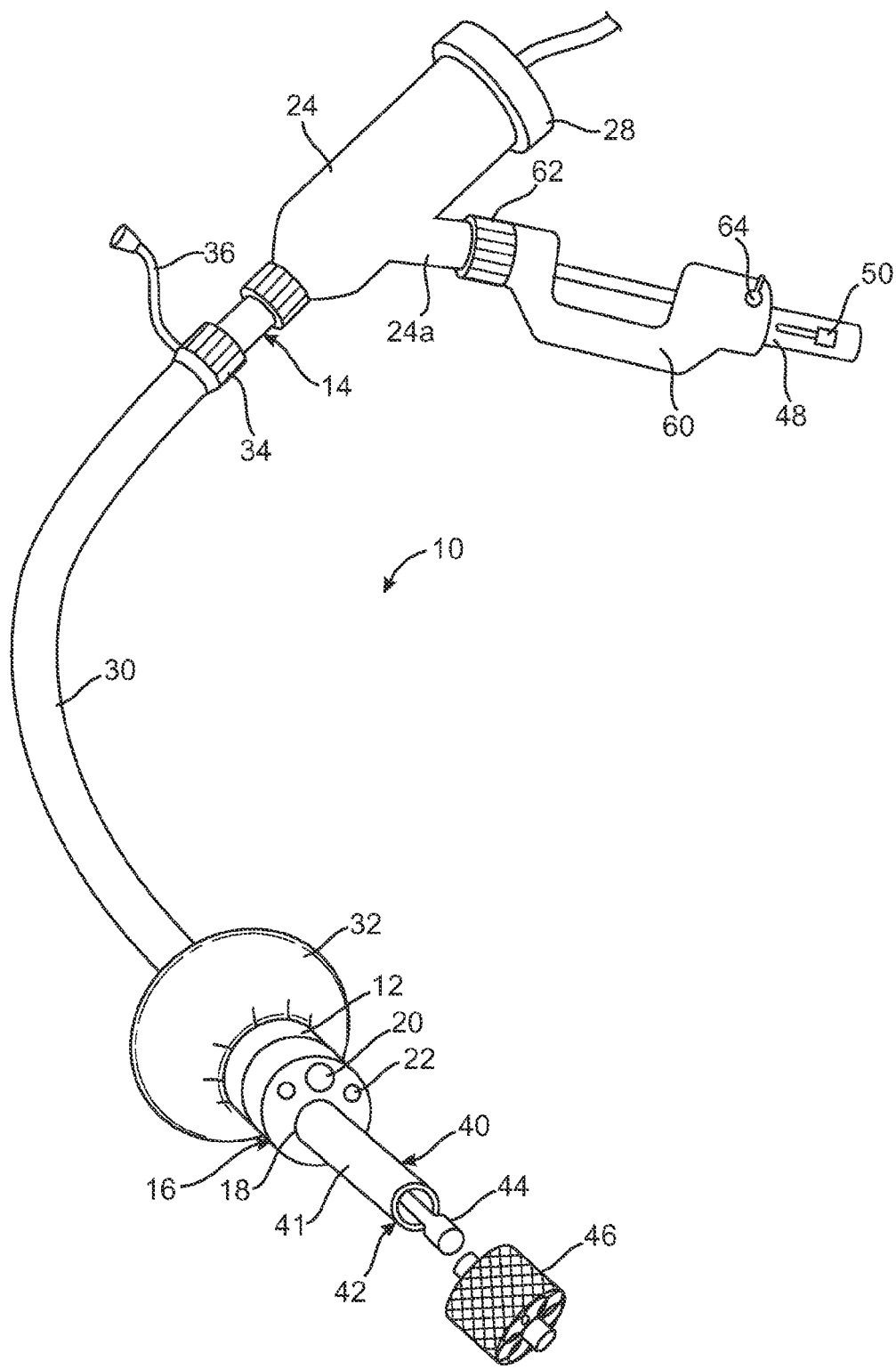
FIG. 1 illustrates an embodiment of a delivery system of the present invention.

The methods of the present invention rely on accessing the target lung tissue segment using an occlusal stent delivery system 10 adapted to be introduced endotracheally into the bronchus of the lung. An exemplary delivery system 10 is illustrated in FIG. 1. As shown, the system 10 comprises a bronchoscope 12 having a proximal end 14, a distal end 16 and at least a working lumen 18 and a scope lumen 20 extending from the proximal end 14 to the distal end 16. Additional lumens, such as an aspiration lumen 22, may also extend therethrough. The bronchoscope 12 also includes a handle 24 disposed near the proximal end 14. The handle 24 is formed to include a sidearm 24a which provides access to the working lumen 18. The handle 24 also includes a connector 28 which permits attachment to an external viewing scope.

It may be appreciated that the bronchoscope 12 included in this embodiment of the system 10 of the present invention may be comprised of any suitable bronchoscope, including conventional bronchoscopes. Conventional bronchoscopes are available from a number of commercial suppliers. Particular bronchoscopes which may be used in the methods and assemblies of the present invention are commercially available from Olympus and Pentax. A principal advantage of the present invention is that it allows a user to modify a conventional bronchoscope for use in delivery of occlusal stents in a convenient and economical manner. However, it may also be appreciated that other instruments or catheters may be used which provide viewing or visualization capabilities.

In this embodiment, the system 10 also includes a sheath 30 having an occlusive member 32 disposed near its distal end, a full description of which is provided in U.S. Pat. No. 6,585,639, assigned to the assignee of the present invention and incorporated by reference for all purposes. The sheath 30 includes a flexible tubular body having a distal end and an occlusive member 32 disposed at or near the distal end of the tubular body. Typically, the occlusive member will be formed from an inflatable elastomeric material which, when uninflated, lies closely over an exterior surface of the distal end of the flexible tubular body. Upon inflation, the material of the occlusive member will simply stretch and permit radial expansion. The elastic nature of the member will permit the member to conform to irregular geometries of a target lung passageway to provide for effective sealing.

The system 10 of FIG. 1 also includes an occlusal stent delivery catheter 40 which is positionable within the working lumen 18 of the bronchoscope 12. The catheter 40 comprises a tubular shaft 41 having a distal end 42, wherein the distal end 42 is extendable beyond the distal end 16 of the scope 12. This may be achieved by slidably advancing the catheter 40 within the working lumen 18. The catheter 40 also includes a positioning rod 44 that is disposed within the tubular shaft 41. The positioning rod 44 is used to expel an occlusal stent 46 from the distal end 42 of the catheter 40, as will be described and illustrated in later sections. The catheter 40 is positionable within the working lumen 18 of the scope 12 by advancement through the sidearm 24a of the handle 24.

The catheter 40 also includes a handle 48 which typically remains outside of the sidearm 24a, though inn some optional configurations an extension of the handle 48 can enter the 24*a* sidearm or the working lumen 18 of the bronchoscope. Both the tubular shaft 41 and the positioning rod 44 are attached to the handle 48 so that gross movement of the handle 48 toward or away from the sidearm 24*a* advances or retracts the catheter 40 within the working lumen 18. To assist in positioning the catheter 40 within the working lumen 18 and to lock portions of the catheter 40 in relation to the scope 12, a clamp connector 60 may be used. The clamp connector 60 may be joined with the sidearm 24*a* by a quick connector 62, however any connecting mechanism may be used. The catheter 40 is advanceable through the clamp connector 60 and the handle 48 is lockable to the clamp connector 60 by a locking mechanism 64. As shown in later figures, the clamp connector can assume other shapes and configurations and can attach to other portions of the bronchoscope in the bronchoscope handle area with a variety of connection mechanisms.

As will be described in later sections, the positioning rod 44 is fixedly attached to the handle 48 and the tubular shaft 41 is slidably attached to the handle 48. Thus, locking of the handle 48 to the clamp connector 60 using locking mechanism 64 in turn locks the positioning rod 44 in relation to the scope 12. The tubular shaft 41 may then be slidably advanced or retracted in relation to the scope 12 and the positioning rod 44 by movement of a handle button 50 on the handle 48. The handle button 50 is fixedly attached to the tubular shaft 41. In this manner, the tubular shaft 41 may be retracted to deploy the occlusal stent 46. It may be appreciated that such a handle button 50 is an example mechanism for achieving such movement of the tubular shaft 41 and that other suitable mechanisms may be used.

Occlusal Stent Delivery Catheter

Figure 2:
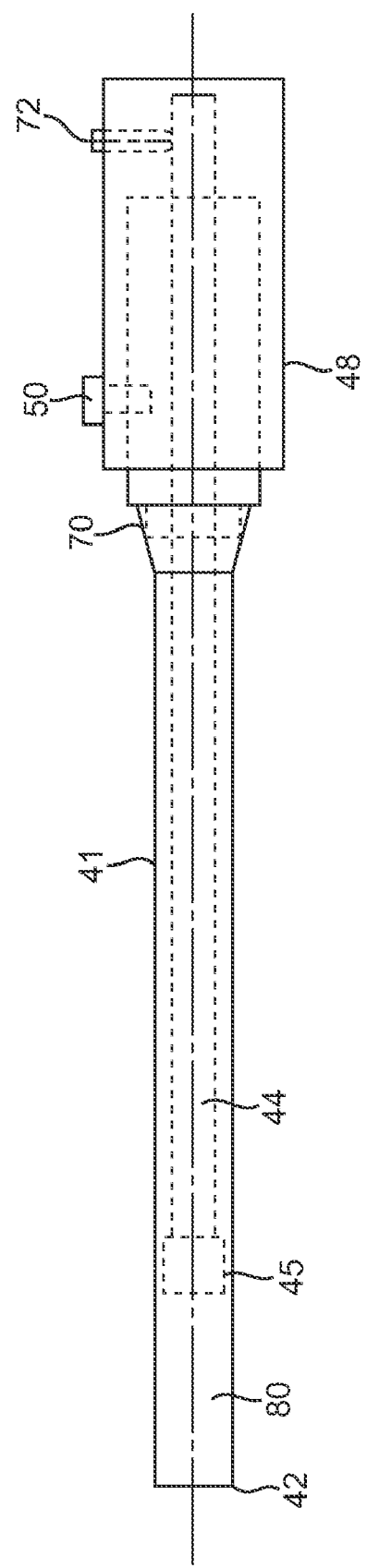
FIG. 2 provides a cross-sectional side view of an embodiment of an occlusal stent delivery catheter.

FIG. 2 provides a cross-sectional side view of an embodiment of an occlusal stent delivery catheter 40. As shown, the catheter 40 includes a positioning rod 44 having a distal end 45, a tubular shaft 41 and a handle 48. The positioning rod 44 is disposed within the tubular shaft 41 and is fixedly attached to the handle 48, in this embodiment by a set screw 72 however any mechanism can be used. The tubular shaft 41 is fixedly attached to a catheter adapter 70 which is sized to fit at least partially within the handle 48. The adapter 70 is slidably attached to the handle 48 with the use of a handle button 50. The handle button 50 is attached to the catheter adapter 70 and shaped to extend through a slot (not shown) in the handle 48 so that the button 50 is able to slide along the slot thereby moving the tubular shaft 41 in relation to the handle 48.

The handle button 50 is positionable so that a receptacle 80 is formed within the tubular shaft 41 between the distal end 45 of the positioning rod 44 and the distal end 42 of the tubular shaft 41. The receptacle 80 is sized to hold an occlusal stent 46 in a contracted form. In preferred embodiments, the maximum axial length of the receptacle 80 is in the range of approximately 20 to 30 mm. Movement of the button 50 along the slot retracts the tubular shaft 41, shortening the axial length of the receptacle 80 until the distal end 45 of the positioning rod 44 meets the distal end 42 of the tubular shaft 41. At this point the receptacle 80 is completely diminished and the occlusal stent 46 is fully exposed and released.

Figure 3:
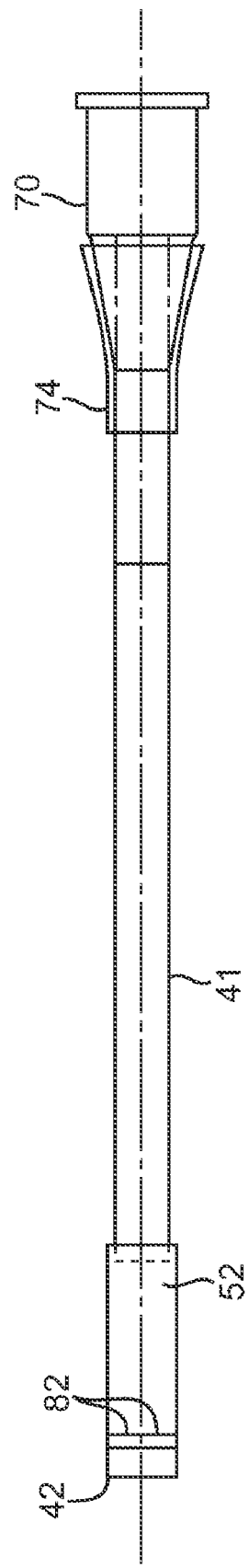
FIG. 3 provides a cross-sectional side view of a tubular shaft of the delivery catheter of FIG. 2.

FIG. 3 provides a cross-sectional side view of the tubular shaft 41 of FIG. 2. As shown, the tubular shaft 41 is connected with a catheter adapter 70. In this embodiment, the connection is achieved with adhesive and heat shrink tubing 74, however any connection methods and materials may be used. In addition, the tubular shaft 41 has a end portion 52 that terminates at the distal end 42 of the shaft 41. In preferred embodiments, the end portion has an axial length in the range of approximately 20 to 120 mm. The end portion 52 is typically comprised of a more flexible material than the remainder of the tubular shaft 41. Such differences in flexibility provide sufficient rigidity throughout the shaft 41 while maintaining maneuverability and kink resistance near the distal end 42. In addition, the end portion 52 typically has a slightly larger diameter than the remainder of the shaft 41 to accommodate the cross-sectional diameter of the collapsed stent 46 while minimizing the diameter of the remainder of the shaft 41 which minimizes friction within the visualization instrument. In preferred embodiments, the overall length of the tubular shaft 41 and adapter 70 is in the range of approximately 30 to 34 inches.

The tubular shaft 41 may include markings 82, as shown. The markings 82 may be comprised of ink or any suitable marking material. Any number of markings 82 may be present, such as a stripe approximately 20 mm from the distal end 41 and another approximately stripe 22.5 mm from the distal end 41. Such markings 82 may be used to assist in positioning the distal end 41 in a passageway. The markings 82 may be observed through the scope 12 as the distal end 41 is manipulated within a lung passageway. Particular markings may be aligned with particular anatomical features to assist in proper placement of the stent 46. For example, when a stent 46 is to be positioned within a relatively large lung passageway, a particular marking such as a distal-most marking may be aligned with the ostium associated with the target lung passageway. Whereas, when a stent 46 is to be positioned within a smaller lung passageway, a different marking, such as a proximal-most marking may be aligned with the ostium associated with the target lung passageway.

Figure 4:
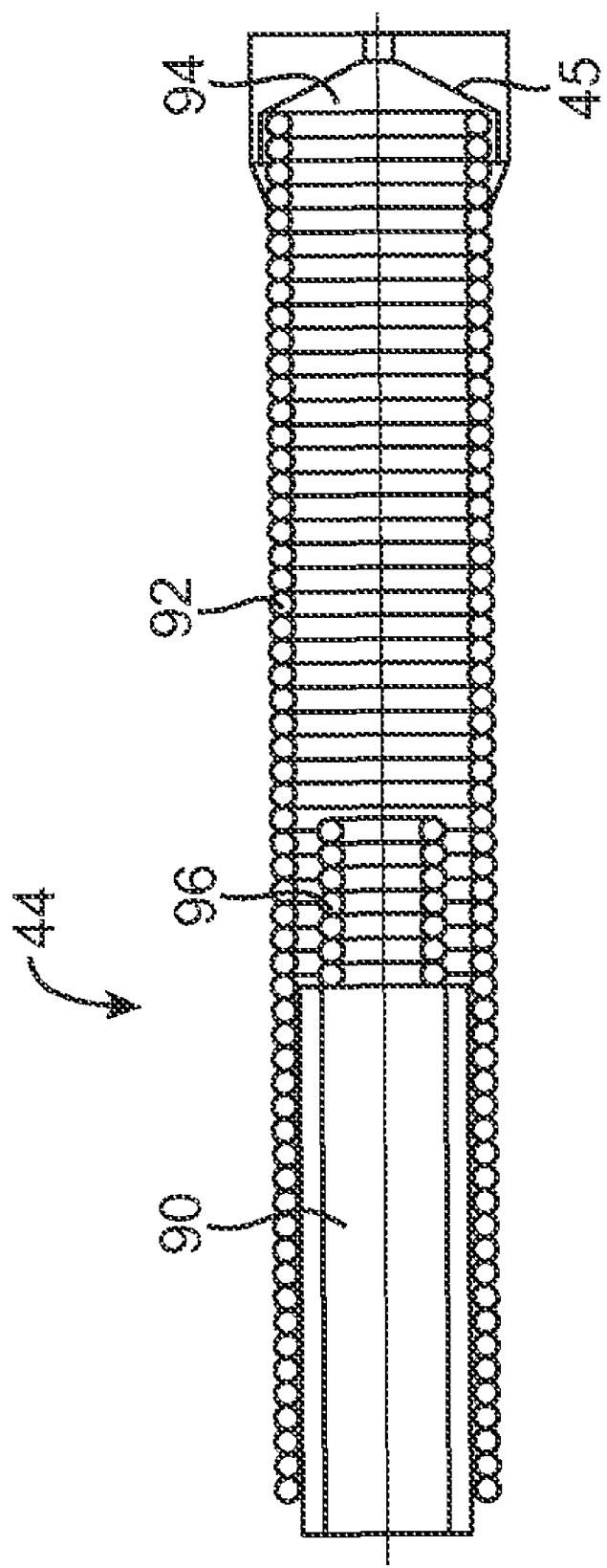
FIG. 4 provides a cross-sectional side view of the positioning rod of FIG. 2.

FIG. 4 provides a cross-sectional side view of the positioning rod 44 of FIG. 2. In this embodiment, the positioning rod 44 is comprised of a main body coil 92 which extends along the length of the rod 44 terminating at a plunger tip 94. Thus, the axial length of the main body coil 92 is in the range of 34 to 40 inches. Typically, the main body coil 92 has an inner diameter in the range of 0.030 to 0.040 inches. The main body coil 92 is comprised of 304 stainless steel wire, however any suitable material may be used. In this embodiment, the plunger tip 94 is comprised of 303 stainless steel and has a maximum outer diameter in the range of 0.075 to 0.085 inches. The positioning rod 44 also includes a push end hypotube 90 disposed within the main body coil 92 opposite to the plunger tip 94. In this embodiment, the hypotube 90 is comprised of 304 stainless steel, however any suitable material may be used. The hypotube 90 has an inner diameter of approximately 0.023 inches and an outer diameter of approximately 0.0355 inches. In addition, the hypotube 90 has an axial length of in the range of 14 to 18 inches. Adjacent to the hypotube 90, within the main body coil 92, is a strain relief coil 96. In this embodiment, the strain relief coil 96 has an axial length in the range of 1 to 2 inches. The strain relief coil 96 is comprised of 304 stainless steel wire, however any suitable material may be used.

Clamp Connector

Figure 5:
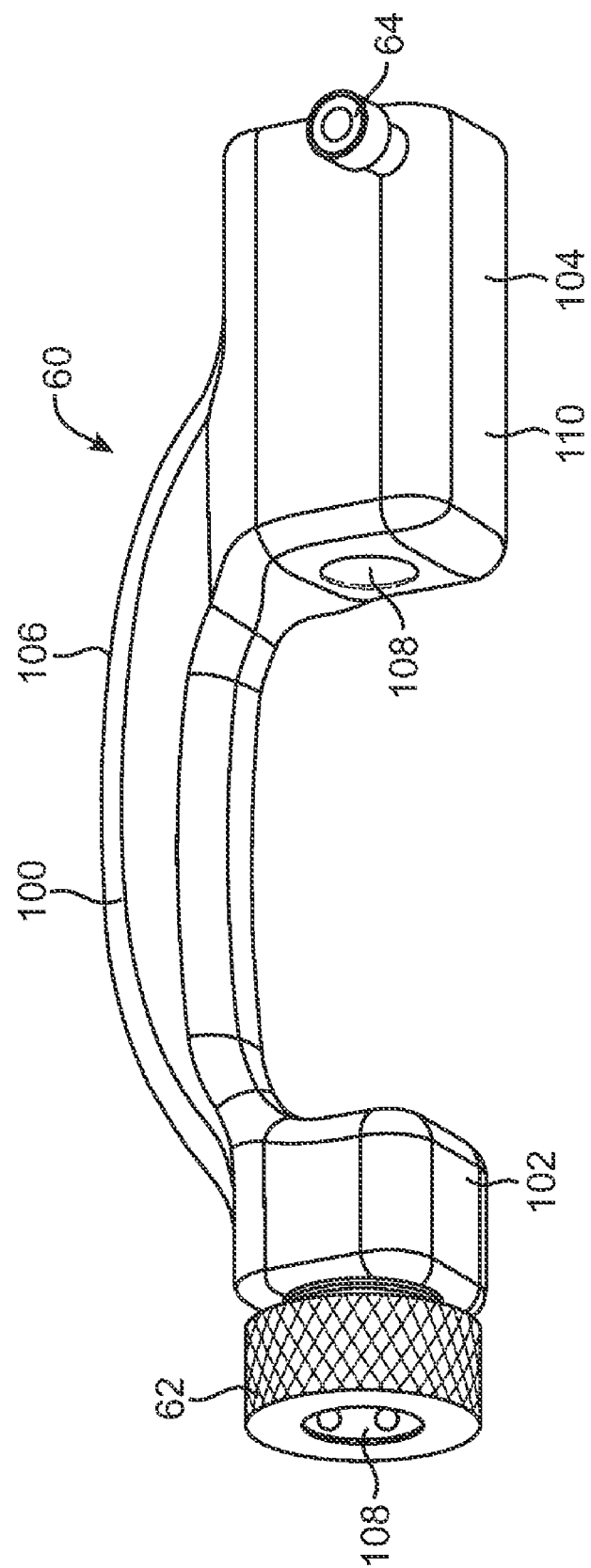

FIG. 5 provides a perspective view of an embodiment of a clamp connector 60. The clamp connector 60 comprises a connector body 100, a quick connector 62, and a locking mechanism 64. The connector body 100 may be comprised of any suitable material, such as a rigid thermoplastic, acetyl butyl styrene (ABS), Delrin® acetal resin, nylon, polycarbonate, metal, or various polymers, to name a few. The connector body 100 may also have any suitable form. In preferred embodiments, the body 100 has a C-shaped form, as shown, having a first end 102, a second end 104 and an arc-shaped arm 106 therebetween. The body 100 has a passageway 108 that extends through the first and second ends 102, 104.

Therefore, an instrument, such as the delivery catheter 40 may be passed through the passageway 108 so that the handle 48 of the catheter 40 is positioned at least partially within at least the second end 104, typically so that the handle button 50 remains outside of the connector body 100. By positioning the handle 48 at least partially within the second end 104, the handle 48 can be locked in relation to the connector 60 with the use of the locking mechanism 64. In some embodiments, the passageway 108 extending through the second end 104 has a split 110. Such a split 110 may be seen in FIG. 5 and FIG. 7. The split 110 allows the passageway 108 through the second end 104 to expand. At least a portion of the handle 48 may then be advanced into the expanded passageway 108. A locking mechanism 64, such as a screw, knob or quick release tensioning lever, may then be tightened, turned or actuated to close the split 110. This in turn applies compressive forces to the handle 48 so that it is held by friction. It may be appreciated, however, that any suitable locking mechanism may be used. The button 50 may then be manipulated to move the tubular shaft 41 of the delivery catheter 40 while the handle 48 is locked to the connector 60.

FIG. 6 provides a top perspective view of an embodiment of a clamp connector 60. Again the clamp connector 60 is shown to have a first end 102, a second end 104 and an arc-shaped arm 106 therebetween. A quick connector 62 is shown joined with the first end 102, and a locking mechanism 64 is shown joined with the second end 104. FIG. 6A illustrates a cross-sectional view along line A-A of FIG. 6. This view illustrates the passageway 108 extending through the quick connector 62, the first end 102, and the second end 104. In addition, this view illustrates the locking mechanism 64. FIG. 7 provides another perspective view of the clamp connector 60 of FIG. 5.

The clamp connector 60 provides a number of advantages. As mentioned, the clamp connector 60 provides a stable platform for introduction of the stent delivery catheter 40 and various other instruments into the working lumen 18 of the bronchoscope 12. As described in this embodiment, the clamp connector fixes the position of the catheter or instrument to the bronchoscope, or optionally fixes a component of the catheter or instrument to the bronchoscope while another component of the catheter or instrument is free to advance or retract within the bronchoscope working lumen while the fixed catheter component remains stationary. In addition, the connector 60 provides for locking of these instruments in a fixed position relative to the bronchoscope. Further, various embodiments of the connector 60 include a quick connector 62 which allows the connector 60 to be quickly and easily attached and detached from the bronchoscope 12. Some embodiments include a side-action quick connector 62 which allows the connector to be attached and detached from a side approach rather than an axial approach. In addition to being more ergonomic, this approach reduces any axial pushing or pulling on the bronchoscope 12 which could inadvertently move the bronchoscope from its desired position. Some embodiments of the connector 60 also include a seal or are attachable with a seal. Commercially available seals include Biopsy Valve (MAJ-210) provided by Olympus America, Inc. (Melville, N.Y.). Such seals may be mounted on the connector 60 for mating with the bronchoscope 12 rather than mounted directly on the bronchoscope 12.

Although the clamp connector 60 may have various forms, the C-shaped form provides particular advantages. The C-shape provides direct access to the passageway 108 through the first end 102 while it is connected to the bronchoscope 12. When the stent delivery catheter or other instrument is passed through the passageway 108, the physician or user can easily grasp the catheter near the first end 102 to assist in advancing the catheter through the bronchoscope 12. This may reduce any risk of kinking the catheter and may assist is passing the catheter through seals within the bronchoscope and/or clamp connector. In addition, such direct access to the passageway 108 through the first end 102 allows the insertion of various instruments without passing the instruments through the second end 104. For example, a syringe may be inserted through the first end 102 to directly inject drugs, etc., into the working lumen 18 of the bronchoscope 12. Likewise suction can be drawn through the working lumen 18 and the first end 102 without drawing suction through the entire connector 60.

Figure 8A:
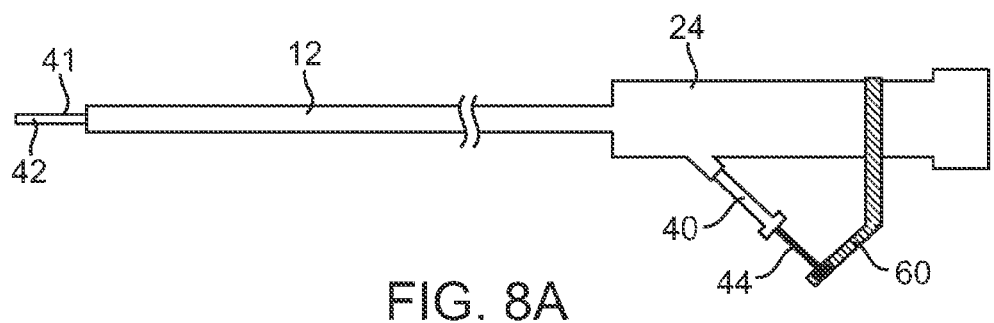
FIGS. 8A-8B illustrate an embodiment of a clamp connector having the form of a bracket.
Figure 8B:
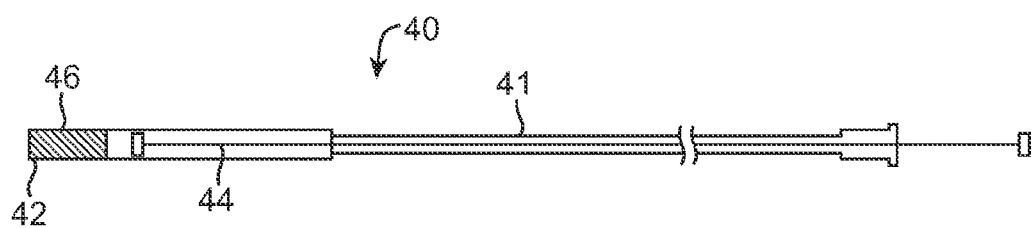

FIGS. 8A-8B illustrate another embodiment of a clamp connector 60. In this embodiment, the clamp connector 60 has the form of a bracket which attaches to the handle 24 of a bronchoscope 12, as shown in FIG. 8A. An occlusal stent delivery catheter 40 may be advanced through the side arm 24a of the bronchoscope handle 24 so that its distal end 42 passes through the bronchoscope 12. The positioning rod 44, which passes through the catheter 40 and extends from the its proximal end, may then be coupled with the clamp connector 60 to lock the positioning rod 44 in a fixed position in relation to the bronchoscope 12. FIG. 8B illustrates the occlusal stent delivery catheter 40 of this embodiment showing the positioning rod 44 extending through the tubular shaft 41. The occlusal stent 46 is shown disposed within the tubular shaft 41 near the distal end 42. Thus, when the positioning rod 44 is locked to the connector 60, the rod 44 is fixed in place. The tubular shaft 41 may then be retracted to expose and deploy the stent 46. By fixing the positioning rod 44 in relation to the bronchoscope 12, there is reduced variability in positioning the stent 46 thereby improving placement accuracy.

Figure 8C:
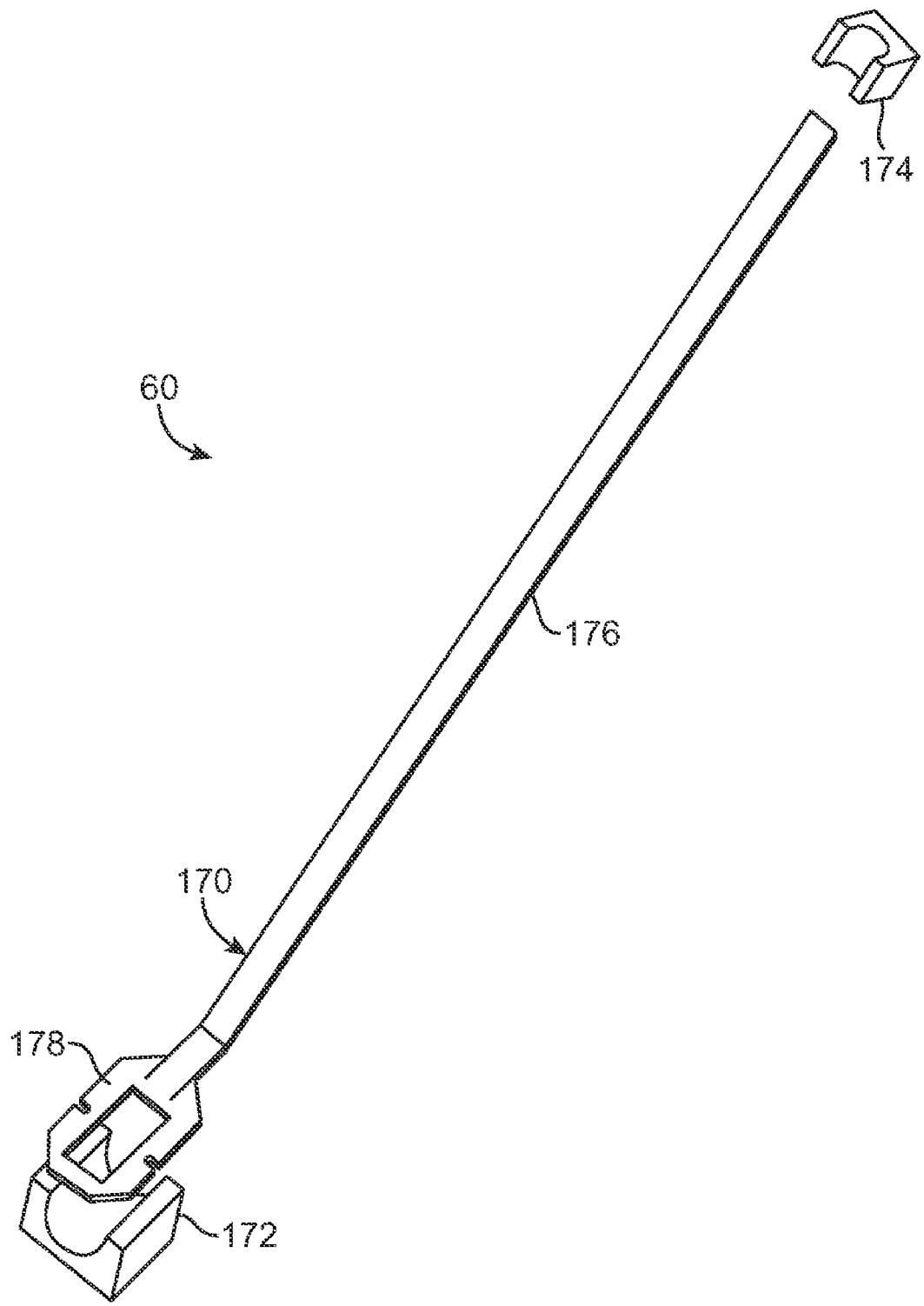
Figure 8D:
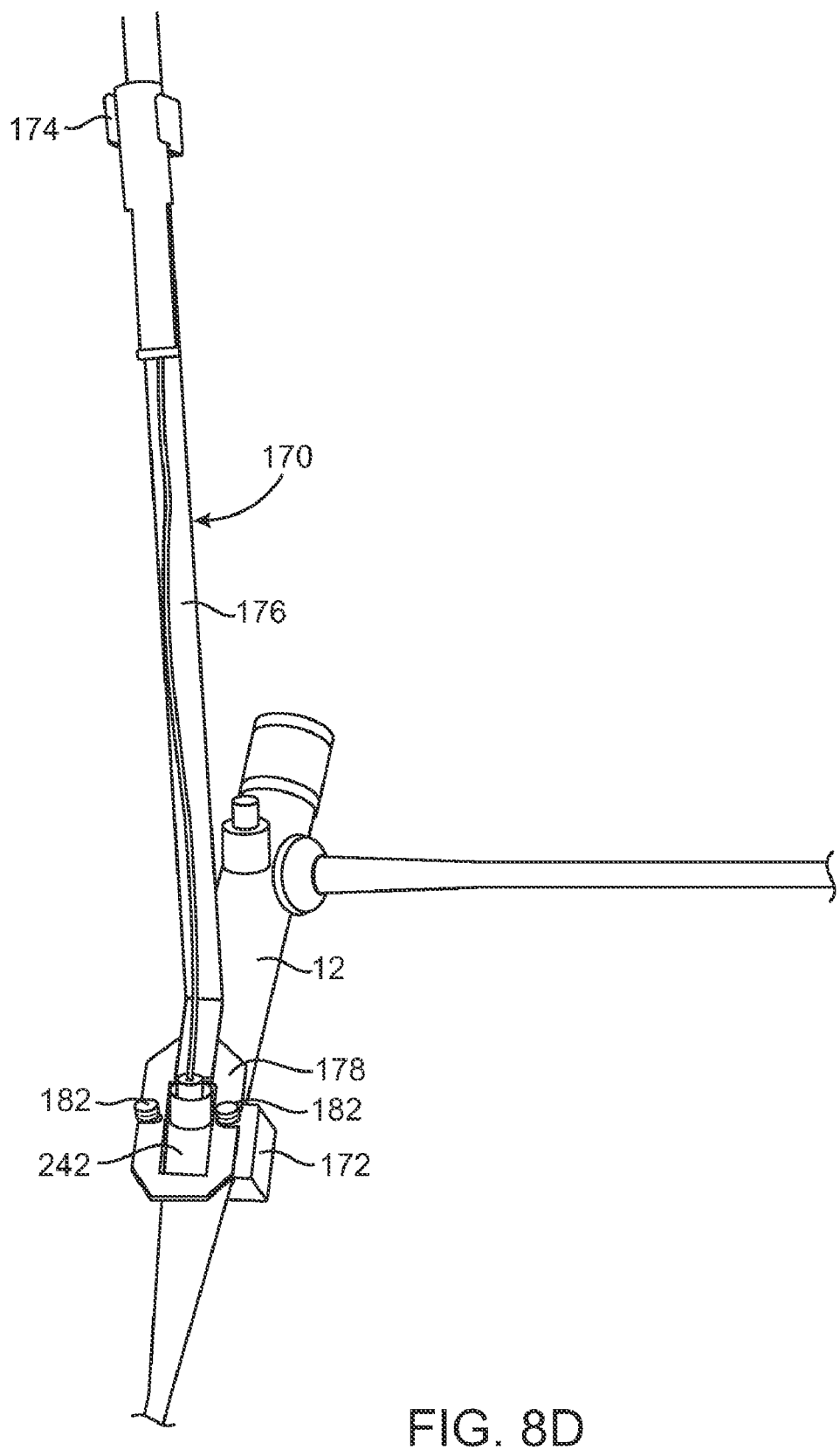

FIGS. 8C-8E illustrate another embodiment of a clamp connector 60. In this embodiment, the clamp connector 60 includes an elongate holder 170, a base 172 and a support 174, as illustrated in FIG. 8C. The elongate holder 170 is comprised of a shaft 176 having a plate 178 (with an aperture 180) attached near one end, and its other end is configured to receive the support 174. Referring to FIG. 8D, the elongate holder 170 is coupleable with a bronchoscope 12. The plate 178 may be positioned against the bronchoscope 12 so that the side arm 24a of the bronchoscope 12 passes through the aperture 180. The base 172 is positioned against the bronchoscope 12 on a side opposite to the side arm 24a so that the base 172 wraps around the bronchoscope 12 as shown. The plate 178 may then be attached to the base 172 with the use of screws 182 or any suitable device. This fixes the clamp connector 60 to the bronchoscope 12. The embodiments described in FIGS. 8A-8D are exemplary and any bracket configuration which attaches to the bronchoscope can be used.

An occlusal stent delivery catheter 40 may then be advanced through the side arm 24a and coupled with the clamp connector 60 to lock the positioning rod 44 in a fixed position in relation to the bronchoscope 12. FIG. 8E provides a side view of the occlusal stent delivery catheter 40 positioned on the clamp connector 60. The plate 178 may be connected with the shaft 176 at any suitable angle so that the shaft 176 holds the catheter 40 in a desired position while allowing manipulation of the bronchoscope 12. The positioning rod 44 passing within the catheter 40 is locked in place by coupling the rod 44 with the support 174. Thus, the rod 44, clamp connector 60 and bronchoscope 12 are in fixed relation to each other. The tubular shaft 41 of the delivery catheter 40 may then be retracted to expose and deploy the stent 46. Again, by fixing the positioning rod 44 in relation to the bronchoscope 12, there is reduced variability in positioning the stent 46 thereby improving placement accuracy.

Occlusal Stent

The occlusal stent delivery system 10 may be used to deliver a variety of occlusal stents 46. Occlusal stents 46 may also be referred to, for example, as occlusal devices, occlusive stents, obstructive devices or plugs. Exemplary occlusal stents 46 are provided in U.S. Pat. No. 6,527,761, and U.S. Provisional Patent Application No. 60/628,649, both assigned to the assignee of the present invention and incorporated by reference for all purposes. A number of embodiments of occlusal stents 46 are comprised of structural supports which expand to anchor the occlusal stent 46 in a lung passageway.

Figure 9:
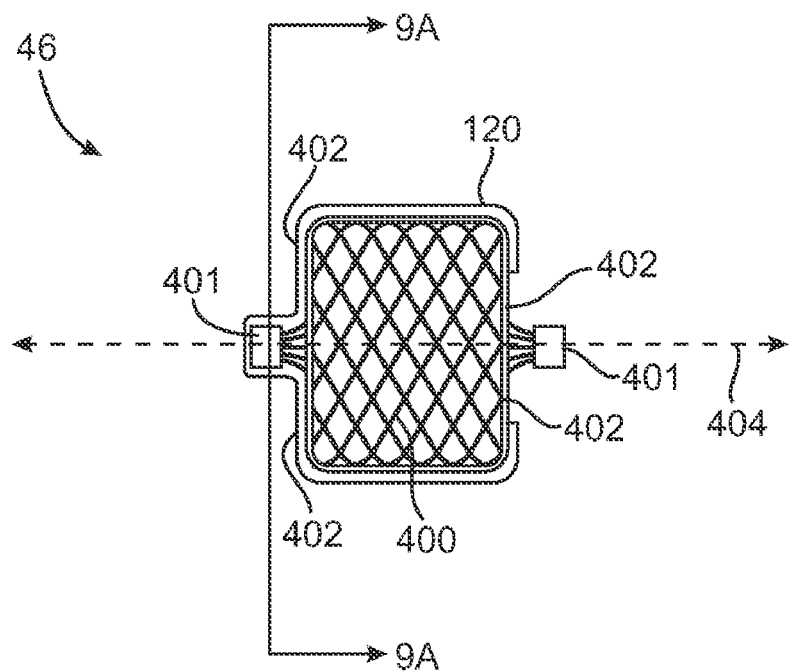
FIGS. 9-9A illustrate an embodiment of an occlusal stent.
Figure 9A:
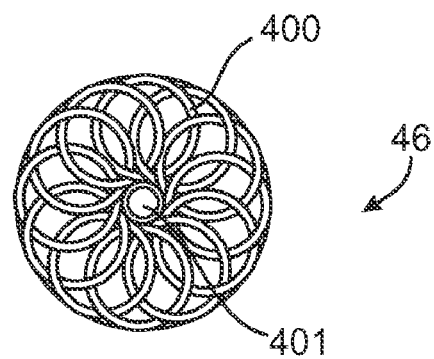

Referring now to FIG. 9 and FIG. 9A, an embodiment of an occlusal stent 46 is shown. Here, the occlusal stent 46 comprises a braid 400. The braid 400 may be comprised of any type of wire, particularly superelastic and/or shape-memory wire, polymer or suitable material. In this embodiment, the braid 400 is comprised of 0.006" Nitinol wire (30-45% CW, oxide/etched surface). The wire braid 400 can be woven from wires having the same diameter, e.g. 24 wires each having a 0.006" diameter, or wires having varied diameters, e.g. 12 wires each having a 0.008" diameter and 12 wires each having a 0.003" diameter. Other numbers of wires and combinations of wire diameters can also be used.

The braid 400 is fabricated on a mandrel having a diameter close in size to the desired diameter of the occlusal stent 46 when unrestrained or in free space. The unrestrained diameter of the stent 46 is typically desired to slightly exceed the internal diameter of the bronchial tube within which it will be placed. Thus, the diameter of the braid 400 may vary depending on the intended usage of the stent 46. Once the braid has been fabricated, the braid is then cut to an appropriate length and shape-set to a desired configuration by heat treatment. The desired configuration generally comprises the ends of the cut length of braid collapsed to form ends or tails, which will be secured and covered by bushings 401, and a portion therebetween having an overall shape conducive to occluding a lung passageway. When other materials, such as Elgiloy® and stainless steel, are used, the wire is formed into the desired configuration using methods different from shape setting methods used for shape memory alloys. After shape-setting, the braid may then be etched to remove oxidation and to form a new passivation layer.

The desired configuration may include a variety of overall shapes, each allowing the occlusal device 46 to perform differently or occlude lung passageways of differing shapes, sizes and configurations. FIG. 9 is a side view of one embodiment of the stent 46 having shoulders 402 which are at an angle which is approximately 90 degrees to a longitudinal axis 404 of the stent 46. Shoulders 402 at such an angle allow maximum contact surface area in relation to length of the stent 46. This is useful when placing the stent 46 into short bronchial segments or take-offs. FIG. 9A is an end view of the embodiment shown in FIG. 9.

Typically, the braid 400 is connected to, encapsulated in, coated or impregnated with a material to prevent flow of gases or liquids through the occlusal device 46, thereby providing an obstruction. In addition, the material may optionally include an antibiotic agent for release into the lung passageway. Examples of obstructive materials include a thin polymer film 120 at least partially encapsulating the occlusal device 46, which may be used to seal against the surface of the lung passageway. Such a design is depicted in FIG. 9. As shown, the film 120 does not completely encapsulate the device 46, leaving a portion of the shoulders 402 exposed. This allows for air to escape from the device 46 when the device is collapsed or contracted. In some embodiments, a bushing 401 located near the exposed area is color coded to signify the area so that the device 46 is loaded in the desired orientation within the delivery catheter 40.

Occlusal Stent Loading

Figure 10A:
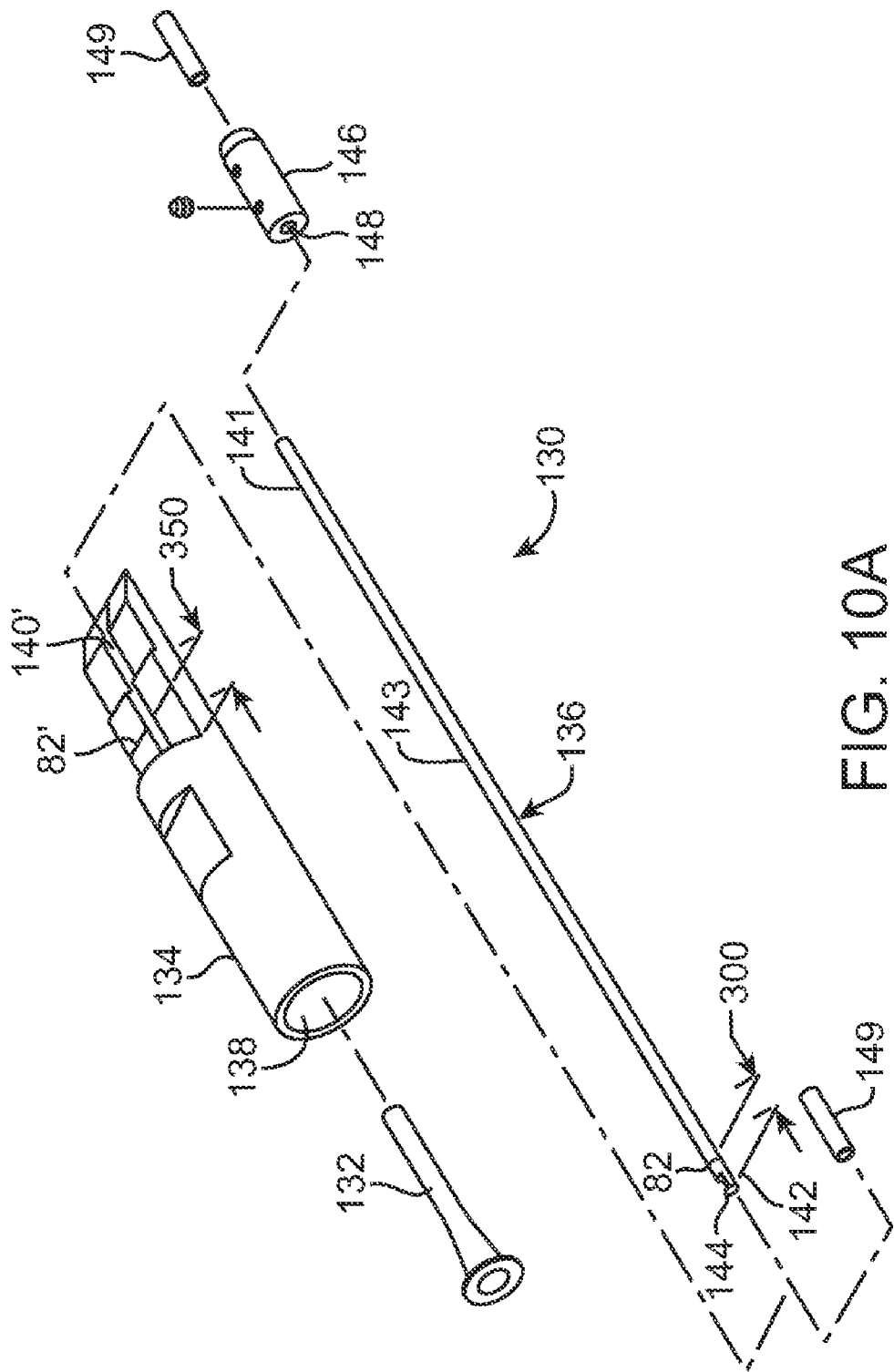
FIG. 10A illustrates an exploded view of an embodiment of a loading system of the present invention.

One or more occlusal stents 46 may be loaded within the delivery system 10 for delivery within a lung passageway. In preferred embodiments, the occlusal stent(s) are loaded into the delivery system 10 with the use of an occlusal stent loading system 130. An embodiment of a loading system 130 of the present invention is illustrated in FIG. 10A. As shown, the system 130 includes a loading body 134, a loading mandrel 136, and a lubricious liner 132. The loading body 134 has a wide-mouthed end 138 and narrow-mouthed end 140, wherein the occlusal stent 46 is loadable into the wide-mouthed end 138 in an expanded configuration and removed from the narrow-mouthed end 140 in a contracted configuration. Thus, the loading body 134 contracts the occlusal stent 46 for loading into the delivery catheter 40. The loading body 134 is also used to load the contracted stent 46 into the delivery catheter 40.

The occlusal stent 46 can be loaded into the loading body 134 with the use of the loading mandrel 136. The mandrel 136 includes a proximal end 141, a distal end 142 and a shaft 143 therebetween. An attachment device 144 is disposed near the distal end 142 which is used to removably attach to the occlusal stent 46. The attachment device 144 may be integral with the mandrel 136 or mounted on, attached to, coupled with the mandrel 136, for example. The attachment device 144 may have any suitable form, including a hook, fork, clasp, fastener, or magnet, to name a few. The mandrel 136 may also include a mandrel grip 146 which has an inner lumen 148 sized for passage of the mandrel 136 therethrough so that the grip 146 may be positioned at any location along the length of the shaft 142. In some embodiments, the grip 146 also serves as a depth stop when loading the stent 46 within the loading body 134. In these embodiments, the grip 146 is preferably positioned in the range of approximately 34 to 38 mm from the proximal end 141 of the shaft 143. The use of the grip 146 as a depth stop will be further described in later sections. In addition, the mandrel 136 may also include one or more mandrel end covers 149.

Figure 10B:
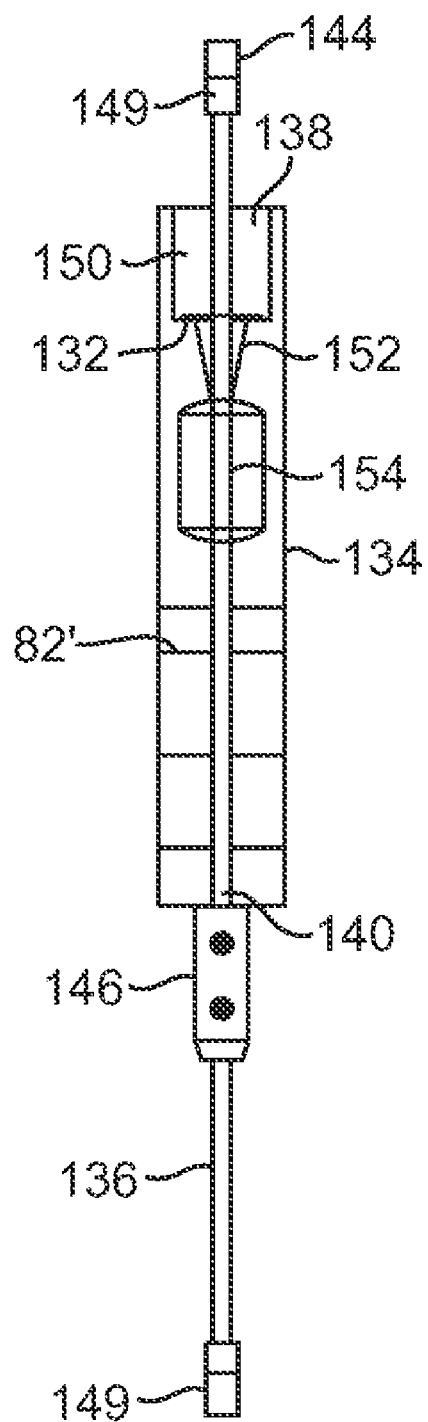
FIG. 10B provides a top view of a loading body having a mandrel positioned therein.

The shaft 143 is sized to be passed through loading body 134. FIG. 10B provides a top view of the loading body 134 having the mandrel 136 positioned therein. As shown, the body 134 includes a loading receptacle 150, a restrictor 152 and a holding tube 154. The lubricious liner 132 is shown inserted into the wide-mouthed end 138 and positioned so that the liner 132 extends through the restrictor 152 and holding tube 154. FIGS. 11A-11D illustrate how an occlusal stent 46 may be prepared for loading into the catheter 40 with the use of these elements of the loading body 134.

Figures 11A, 11B, 11C:
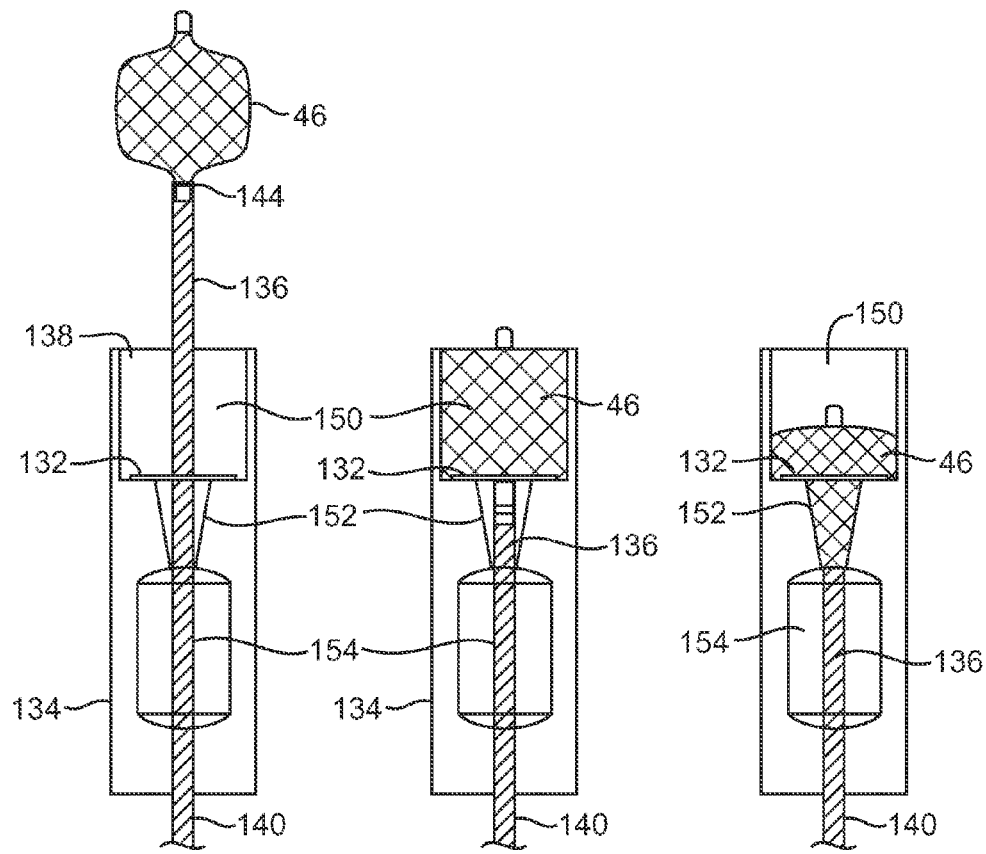
FIGS. 11A-11D illustrate loading of an occlusal stent into the loading system.
Figure 11D:
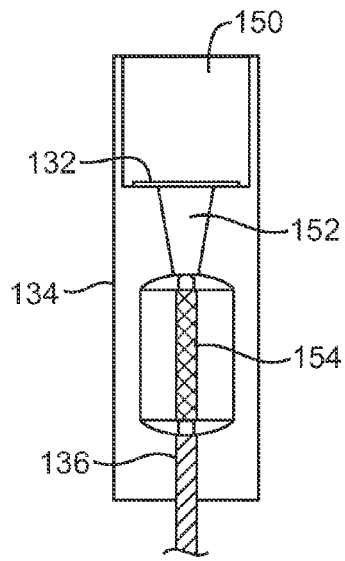

FIG. 11A illustrates a portion of the loading body 134 wherein the distal end 142 of the loading mandrel 136 is shown passed through the narrow-mouthed end 140 to and beyond the wide-mouthed end 138. The attachment device 144 is shown attached to the occlusal stent 46. In this embodiment, the attachment device 144 comprises a fork which releasably joins with the occlusal stent 46. The mandrel 136 is then retracted, drawing the occlusal stent 46 into the loading receptacle 150 at the wide-mouthed end 138, as shown in FIG. 11B. Further retraction of the mandrel 136 pulls the occlusal stent 46 into the restrictor 152 which gradually collapses the stent 46, as shown in FIG. 11C. As the stent 46 collapses, air within the stent 46 is forced out toward the narrow-mouthed end 140. Still further retraction of the mandrel 136 pulls the contracted stent 46 into the holding tube 154, as shown in FIG. 11D. The liner 132 serves to reduce any friction between the stent 46 and the loading body 134 as the stent 46 is collapsed and passed through the loading body 134. Thus, the liner 132 may be comprised of any suitable material which reduces friction, such as Teflon®. It may be appreciated that the liner 132 may alternatively be integral with the loading body 134 or may have the form of a coating on surfaces of the loading body 134. The occlusal stent 46 is now ready for loading into the delivery catheter 40.

It may be appreciated that the loading system 130 may be constructed from any suitable materials. Preferably, the loading body 134 is constructed from a material which allows visibility of the stent 46 throughout the loading process. This may ensure that the stent 46 is properly loaded within the loading body 134. Alternatively or in addition, a variety of markings 82, 82' may be used to ensure proper loading. For example, as shown in FIG. 10A, the mandrel 136 may include a marking 82, such as a line of ink, on the shaft 143 a desired distance from the distal end 142. In preferred embodiments, the marking 82 is disposed approximately 0.3 inches from the distal end 142. The loading body 134 then includes a corresponding marking 82' near the narrow-mouthed end 140, approximately 0.35 inches from the holding tube 154. When the mandrel 136 is retracted so that the marking 82 on the shaft 143 is aligned with the marking 82' on the loading body 134, the occlusal stent 46 is properly positioned within the holding tube 154.

Figures 11E, 11F:
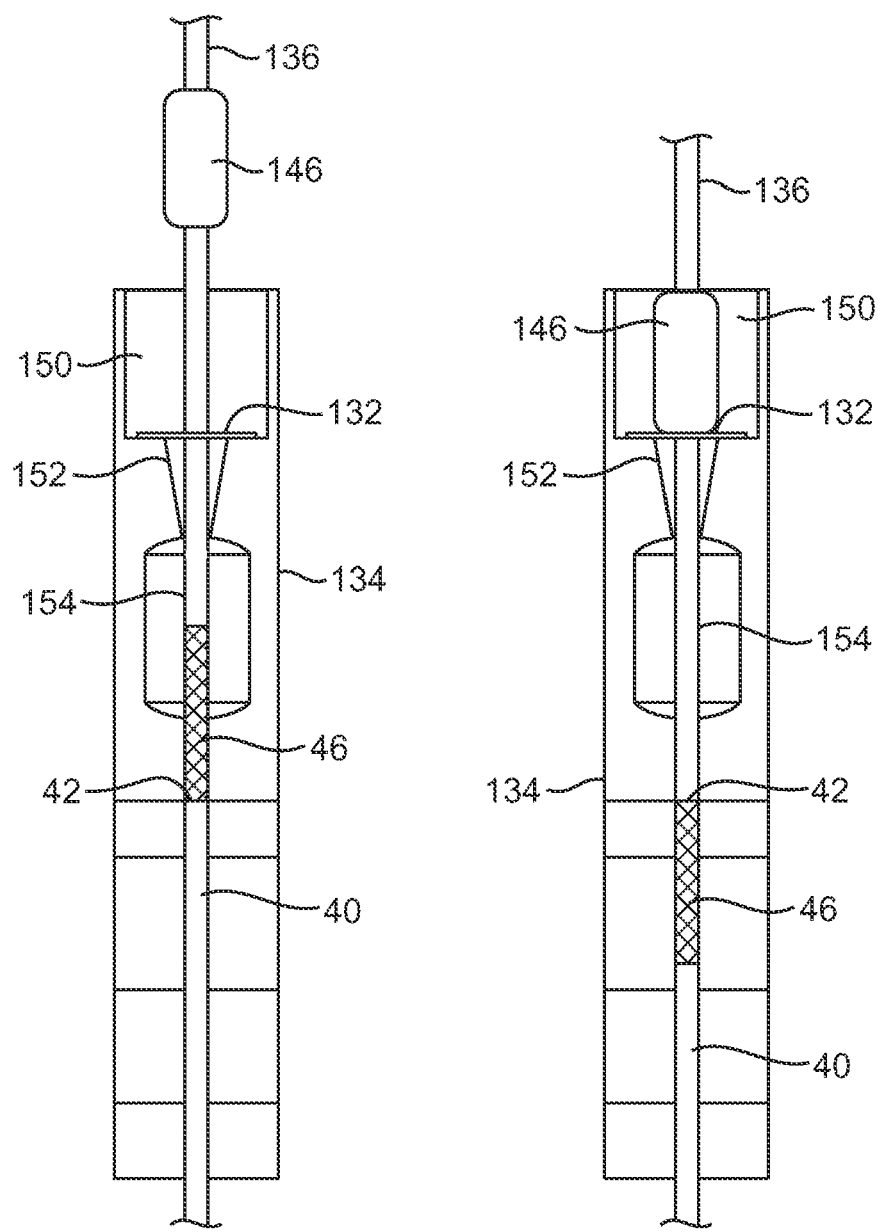
FIG. 11E-11G illustrate transferring of an occlusal stent to a delivery catheter.
Figure 11G:
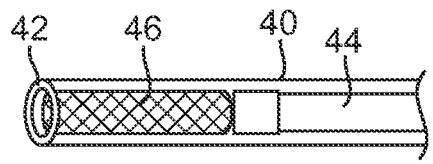

The occlusal stent 46 may then be transferred to the delivery catheter 40, as illustrated in FIGS. 11E-11G. FIG. 11E illustrates the delivery catheter 40 positioned against the holding tube 154 of the loading body 134. The loading mandrel 136 or any other suitable instrument is used to transfer the occlusal stent 46 to the distal end 42 of the delivery catheter 40. As shown, the proximal end 141 of the loading mandrel 136 is advanced through the loading receptacle 150 and the restrictor 152 until it contacts the occlusal stent 46. Continued advancement of the loading mandrel 136 pushes the occlusal stent 46 from the holding tube 154 and into the catheter 40. FIG. 11F illustrates the loading mandrel 136 fully advanced so that the occlusal stent 46 is fully loaded within the catheter 40. In some embodiments, the mandrel grip 146 assists in proper placement of the stent 46 within the holding tube 154 by serving as a depth stop for the loading mandrel 136. The grip 146 is sized so that it may be advanced into the loading receptacle 150 but cannot be advanced into the restrictor 152, thus serving as a depth stop. The grip is positioned along the length of the mandrel 136 so that when the grip 146 is positioned against the restrictor 152, as shown in FIG. 11F, the stent 46 is properly positioned within the holding tube 154. FIG. 11G illustrates the distal end 42 of the catheter 40 removed from the loading body 134 and having the occlusal stent 46 loaded inside.

It may be appreciated that the loading system 130 may be adapted to load more than one occlusal stent 46. For example, the holding tube 154 may be lengthened to hold two, three, four, five or more stents 46 at one time. The stents 46 may be individually loaded into separate delivery catheters, simultaneously loaded into a single delivery catheter or loaded in groups into a few catheters.

Figure 12A:
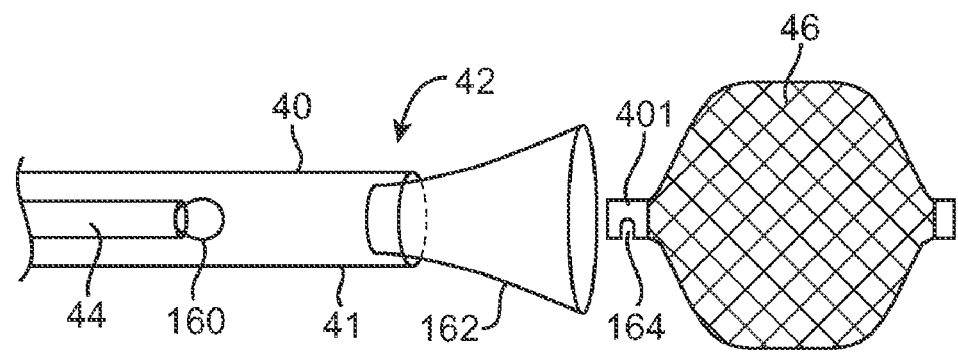
FIGS. 12A-12C illustrate an alternative method of loading a delivery catheter with an occlusal stent.
Figure 12B:
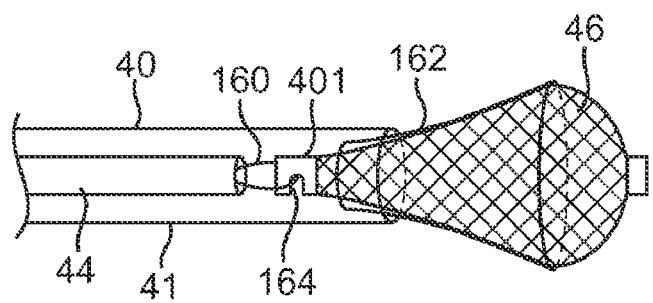
Figure 12C:
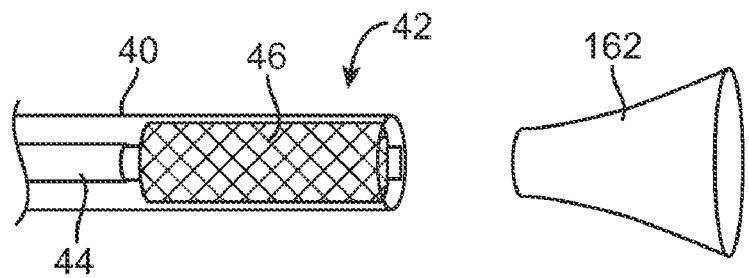

FIGS. 12A-12C illustrate an alternative method of loading a delivery catheter 40 with an occlusal stent 46. In this embodiment, one or more stents are loaded directly into the distal end 42 of the delivery catheter 40. As shown in FIG. 12A, the delivery catheter 40 includes a positioning rod 44 having a grasping device 160 disposed at its tip. In this example, the grasping device 160 has the shape of a ring, loop, hoop or circle. The device 160 may be comprised of any suitable material, such as wire, polymer, thread, fiber, or suture, to name a few. A restricting insert 162 is positioned at least partially within the distal end 42, such as shown. Optionally it can be appreciated that the restricting insert 162 can be of the type that engages with an outer surface or edge of the distal end 42 so that the insert 162 is not at least partially within the distal end 42. The restricting insert 162 is used to assist in collapsing and loading the stent 46 within the distal end 42 of the catheter 40. This is achieved by retracting the tubular shaft 41 so that the grasping device 160 can be removably attached to a bushing 401 on an occlusal stent 46. As shown in FIG. 12A, at least one of the bushings 401 includes a notch 164 which is mateable with the grasping device 160. As shown in FIG. 12B, the grasping device 160 attaches to the bushing 401 and draws the occlusal stent 46 through the restricting insert 162 and into the tubular shaft 41 of the catheter 40. FIG. 12C shows the distal end 42 of the catheter 40 having the occlusal stent 46 loaded inside and the restricting insert 162 removed.

Figure 13A:
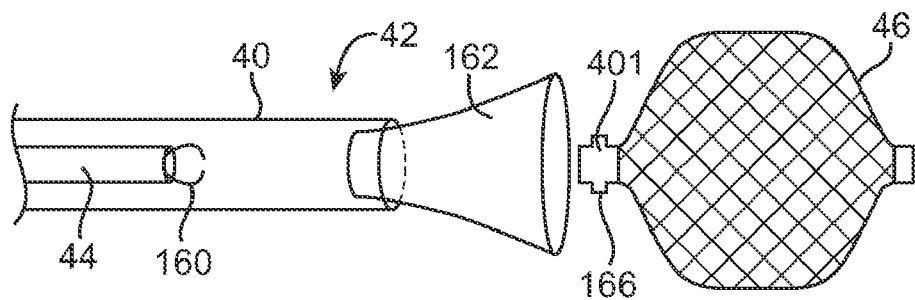
FIGS. 13A-13C illustrate an similar method of loading a delivery catheter to that of FIGS. 12A-12C.
Figure 13B:
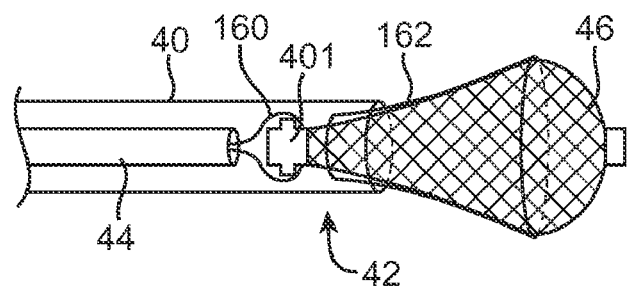
Figure 13C:
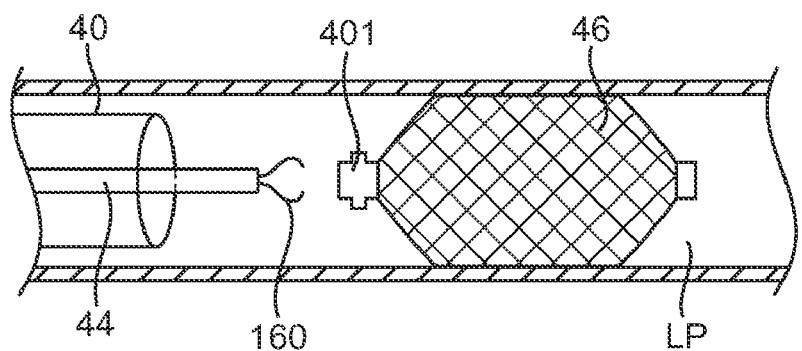

FIGS. 13A-13C illustrate an similar method of loading a delivery catheter 40 with an occlusal stent 46. As shown in FIG. 13A, the delivery catheter 40 includes a positioning rod 44 having a grasping device 160 disposed at its tip. In this example, the grasping device 160 has the shape of a pincher or claw. The tubular shaft 41 is retracted so that the grasping device 160 pinch onto a bushing 401 on an occlusal stent 46. As shown in FIG. 13A, at least one of the bushings 401 includes one or more protrusions 166 which the grasping device 160 is able to utilize in grasping. As shown in FIG. 13B, the grasping device 160 grasps the bushing 401 and draws the occlusal stent 46 through the restricting insert 162 and into the tubular shaft 41 of the catheter 40. A restricting insert 162 is positioned at least partially within the distal end 42, as shown. The restricting insert 162 is used to assist in collapsing the stent 46 and loading the stent 46 within the distal end 42 of the catheter 40. The grasping device 160 may also be used to retrieve or adjust an occlusal stent 46 which has been deployed in a lung passageway LP, as illustrated in FIG. 13C. As shown, the distal end 42 of the catheter 40 may be retracted to expose the grasping device 160 which can be used to grasp onto the bushing 401 of the occlusal stent 46. The stent 46 may then be manipulated by the grasping device 160. In some methods, the occlusal stent 46 may be deployed in a more distal position within the lung passageway LP than desired so that the stent 46 may then be pulled proximally to a desired position with the use of the grasping device 160.

It may further be appreciated that delivery catheters 40 of the present invention may alternatively be provided to a physician or user in a preloaded state wherein one or more occlusal stents 46 are provided within the catheters 40, ready for delivery. Further, it may be appreciated that automatic loading systems may be provided, or systems in which the stent is pre-connected to the catheter rod but not yet loaded into the catheter receptacle.

Methods of Use

The occlusal stent delivery system 10 of the present invention may be used for a variety of therapeutic procedures, preferably for performing "endobronchial volume reduction" (EVR). EVR is a non-surgical technique for isolating and occluding diseased lobar and sub-lobar regions of a patient's lung. An isolated region will be a portion (usually not the whole) of the right or left lung, and volume reduction will be accomplished by evacuating the region and occluding a bronchial passage within or leading to the region with an occlusal stent 46. One or more bronchial passageways within or leading to the region may be occluded while the region is evacuated, as will be described.

Initially, the bronchoscope 12 is separate from the sheath 30 and the distal end 16 of the scope 12 is then introduced through a luer or other proximal connector 34 of the sheath 30. Referring back to FIG. 1, the distal end 16 is advanced until the occlusive member 32 is disposed at a desired position along the length of the scope 12. At that point, the luer or other connector 34 is then tightened on to the scope 12. A suitable monitor may then be connected to the bronchoscope 12 in a conventional manner. Inflation of member 32 may be effected through an inflation tube 36, typically using a pressurized air or other gas source.

Figure 14A:
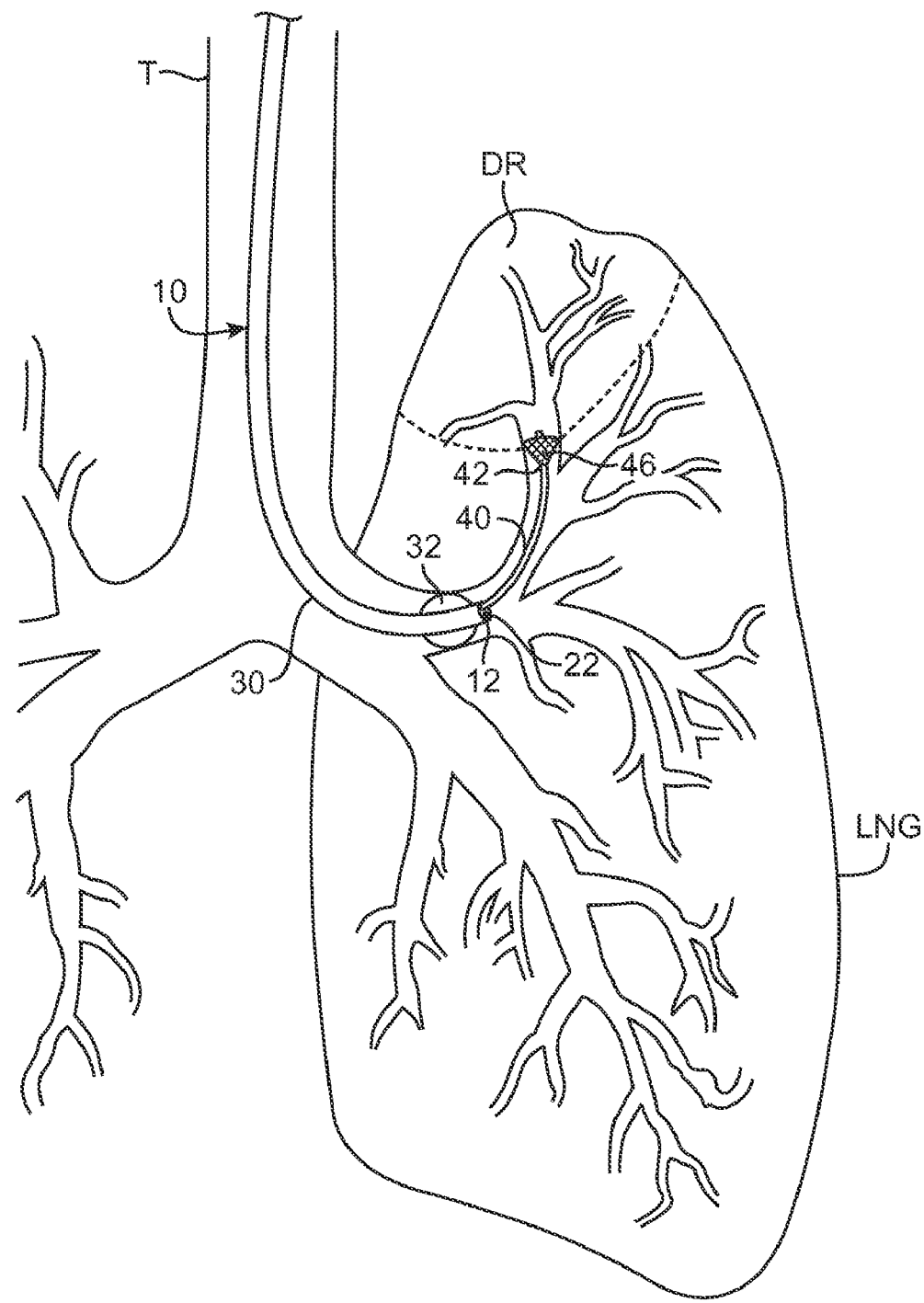
FIGS. 14A-14C illustrates methods of using the occlusal stent delivery system of the present invention within lung passageways.

Referring now to FIG. 14A, the assembly of the sheath 30 and bronchoscope 12 may be introduced through the trachea T to a target location in a patient's lung LNG. The sheath-bronchoscope assembly 30/12 is introduced so that the occlusive member 32 reaches a desired location, in this example a major takeoff in the left lung. At that point, the member 32 may be inflated. During the advancement and after inflation of the member 32, viewing through the bronchoscope 12 may be accomplished through the monitor connected to the scope 12.

While the member 32 is inflated, lung segments beyond the member 32 may be evacuated by applying vacuum suction through an aspiration lumen 22 in the bronchoscope 12. The occlusal stent delivery catheter 40 (having an occlusal stent 46 pre-loaded within its distal end 42) is then advanced through the working lumen 18 of the bronchoscope 12. Forward imaging by the bronchoscope 12 is effected by illuminating through light fibers within the scope lumen 20 and detecting an image through a lens at the distal end 16 of the bronchoscope 12. The resulting image can be displayed on conventional cathode-ray or other types of imaging screens. In particular, forward imaging permits a user to selectively place the catheter 40 through a desired route through the branching bronchus. It may be appreciated, however, that as an alternative positioning could be done solely by fluoroscopy.

In any case, referring again to FIG. 14A, the delivery catheter 40 is then advanced until its distal end 42 reaches a region in the bronchus or lung passageway which leads directly into a diseased region DR. The delivery catheter 40 is advanced through the working lumen 18 of the bronchoscope 12 via the passageway 108 of the clamp connector 60 attached to the side arm 24a, as previously described. Once the distal end 42 of the catheter 40 is positioned in a desired location within the lung passageway, the catheter 40 is locked in place with the use of the locking mechanism 64 on the clamp connector 60. The occlusal stent 46 may then be deployed in the passageway. Recall, the occlusal stent 46 is pre-loaded in a compressed or collapsed state within an interior lumen of the delivery catheter 40. The occlusal stent 46 is deployed by retracting the tubular shaft 41 of the delivery catheter 40. This is achieved by sliding the handle button 50 on the handle 48 of the catheter 40, as previously described. As the tubular shaft 41 retracts, the positioning rod 44 holds the occlusal stent 46 in place. Thus, the occlusal stent 46 is gradually exposed. If the stent 46 is self-expanding, for example by tension or shape-memory, the stent 46 will expand and anchor itself in the passageway as the occlusal stent 46 is exposed, as shown in FIG. 14A. If the occlusal stent 46 is not self-expanding, it may be expanded with the use of a balloon or other mechanism provided by the delivery catheter 40, a catheter or device delivered through the catheter 40, or another device.

Figure 14B:
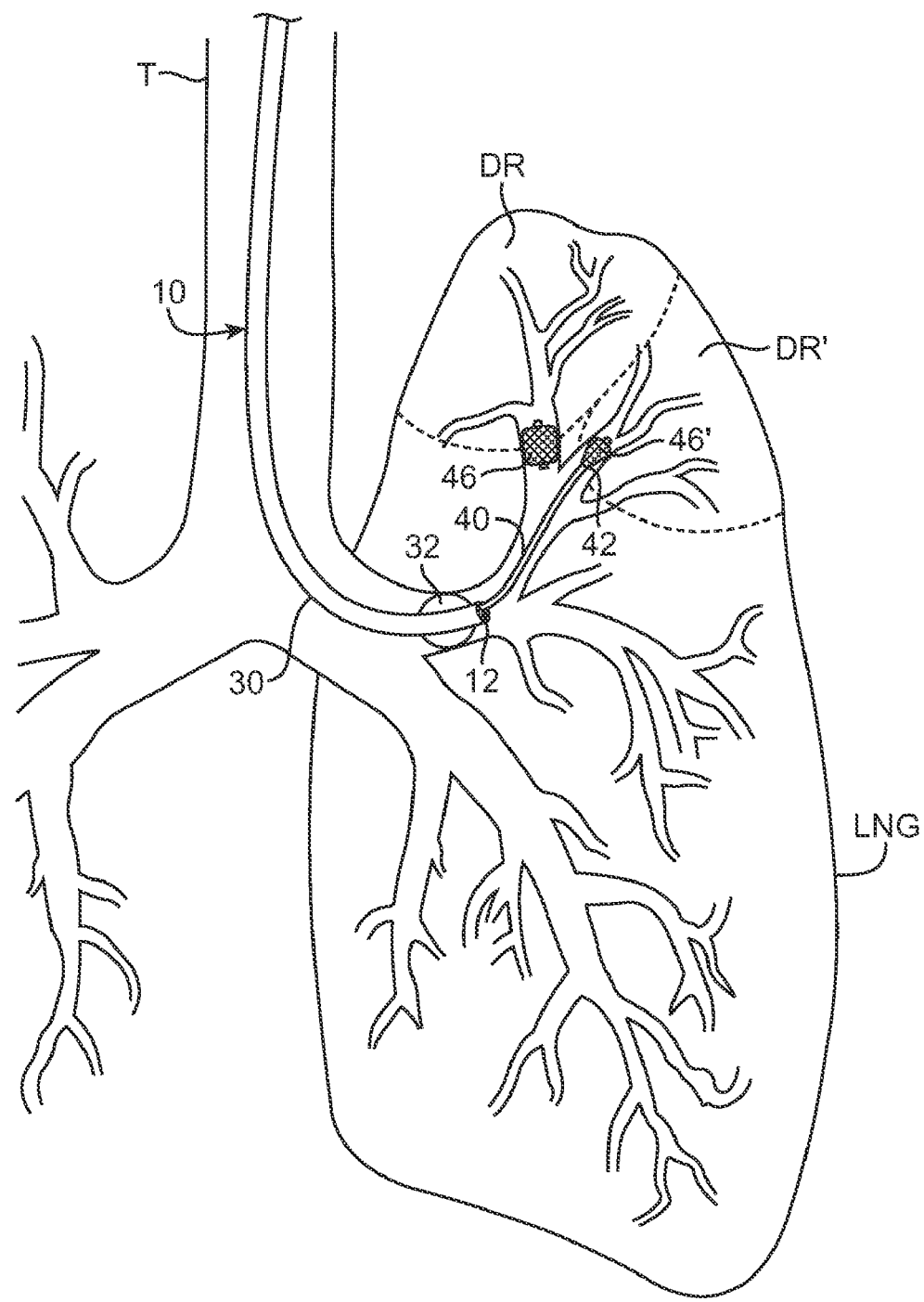

While the sheath 30 and occlusive member 32 are in place, additional occlusal stents may be positioned within the evacuated lung passageways beyond the member 32. The delivery catheter 40 may be removed and loaded with a second occlusal stent 46' for reintroduction, or the delivery catheter 40 may be removed and replaced with another delivery catheter 40 that has already been preloaded with a second occlusal stent 46'. Referring now to FIG. 14B, the delivery catheter 40 is then advanced until its distal end 42 reaches a region in the bronchus or lung passageway which leads directly into a second diseased region DR'. Again, the delivery catheter 40 is advanced through the working lumen 18 of the bronchoscope 12 with the use of the clamp connector 60 attached to the side arm 24a, as previously described. Once the distal end 42 of the catheter 40 is positioned in a desired location within the lung passageway, the catheter 40 is locked in place with the use of the locking mechanism 64 on the clamp connector 60. The second occlusal stent 46' may then be deployed in the passageway. The second occlusal stent 46' is deployed by retracting the tubular shaft 41 of the delivery catheter 40. As the tubular shaft 41 retracts, the positioning rod 44 holds the second occlusal stent 46' in place. If the stent 46' is self-expanding, the stent 46' will expand and anchor itself in the passageway as the second occlusal stent 46' is exposed, as shown in FIG. 14B.

Figure 14C:
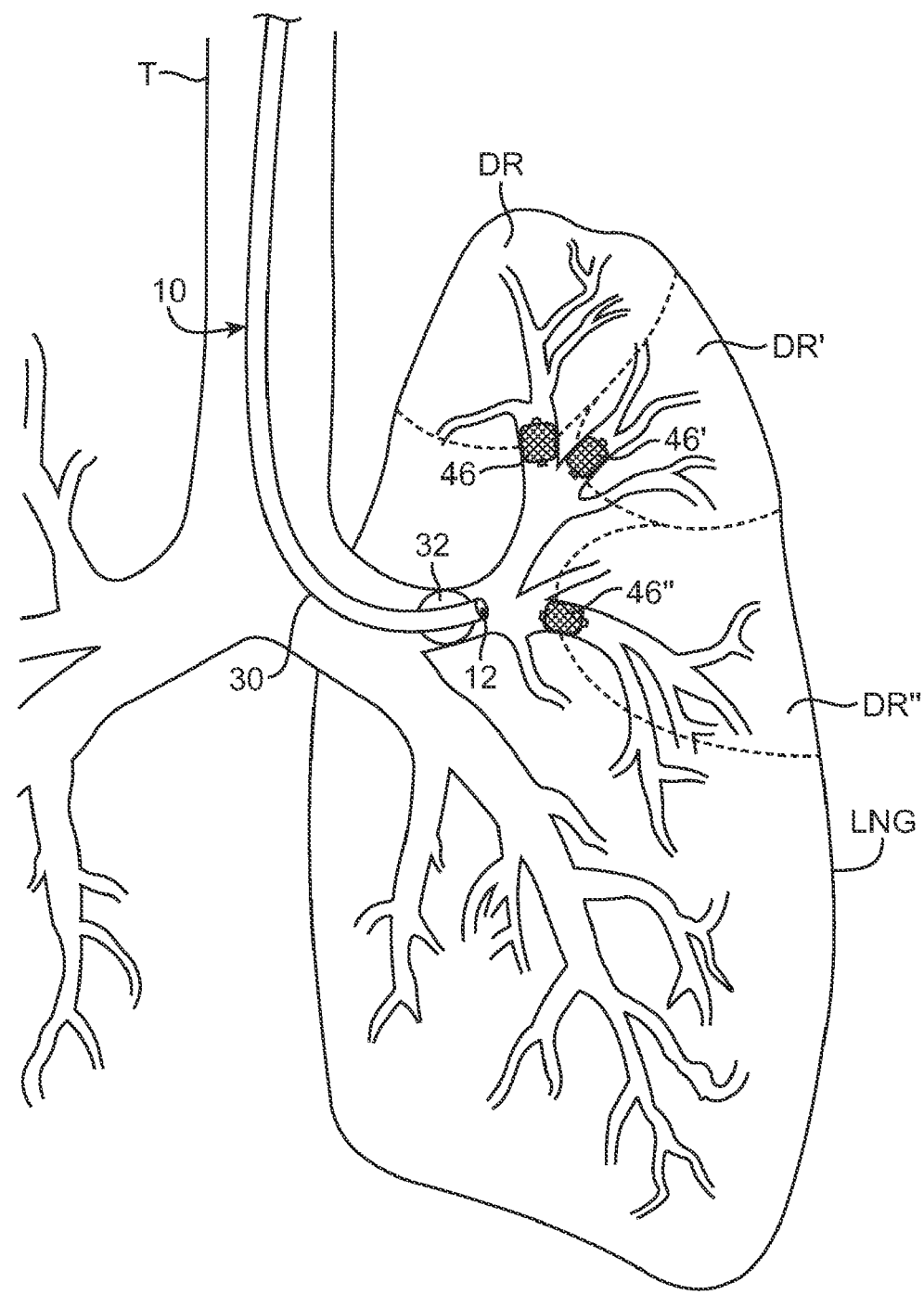

Further, while the sheath 30 and occlusive member 32 are in place, any number of additional occlusal stents may also be positioned within the evacuated lung passageways beyond the member 32. Again, the delivery catheter 40 may be removed and loaded with a third occlusal stent 46" for reintroduction, or the delivery catheter 40 may be removed and replaced with another delivery catheter 40 that has already been preloaded with a third occlusal stent 46" (thus, it may be efficient to utilize two delivery catheters 40 so that one catheter 40 may be preloaded with an occlusal stent while the other is in use). The delivery catheter 40 is then advanced until its distal end 42 reaches a region in the bronchus or lung passageway which leads directly into a third diseased region DR". Again, the delivery catheter 40 is advanced through the working lumen 18 of the bronchoscope 12 with the use of the clamp connector 60 attached to the side arm 24a, as previously described. Once the distal end 42 of the catheter 40 is positioned in a desired location within the lung passageway, the catheter 40 is locked in place with the use of the locking mechanism 64 on the clamp connector 60. The third occlusal stent 46" may then be deployed in the passageway, as shown in FIG. 14C.

The occlusive member 32 may then be deflated and the delivery system 10 removed, leaving the occlusal devices 46, 46', 46" behind wherein each occlusal device isolates and occludes a diseased region DR, DR', DR", respectively.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A method of introducing an implant into a lung passageway, the method comprising:
   introducing a viewing scope into the lung passageway;
   introducing a delivery catheter holding the implant into a lung passageway via the viewing scope, wherein the delivery catheter comprises a distal end with an outer surface having a marking configured as a stripe thereon which is visible through the viewing scope when the distal end of the catheter is in the passageway;

viewing the marking on the catheter to assist in positioning the distal end of the catheter in the lung passageway; and deploying the implant.

2. The method of claim 1, further comprising positioning the delivery catheter within the lung passageway prior to deploying the implant.

3. The method of claim 2, wherein the positioning step comprises aligning the marking with a target feature within the lung passageway.

4. The method of claim 3, wherein the target feature is an ostium.

5. The method of claim 1, wherein the implant is an occlusal stent.

6. The method of claim 1, wherein the delivery catheter further comprises a second marking.

7. The method of claim 6, further comprising viewing the marking and the second marking and aligning the marking and the second marking with respect to a target feature within the lung passageway.

* * * * *